US008741916B2

(12) United States Patent  
Bignan et al.

(10) Patent No.: US 8,741,916 B2
(45) Date of Patent: Jun. 3, 2014

(54) 1,3,8-TRISUBSTITUTED-1,3,8-TRIAZA-SPIRO[4.5]DECAN-4-ONE DERIVATIVES AS LIGANDS OF THE ORL-1 RECEPTOR

(75) Inventors: Gilles C. Bignan, Bridgewater, NJ (US); Dennis J. Hlasta, Doylestown, PA (US); Richard R. Ryan, Yardley, PA (US)

(73) Assignee: Janssen Pharmaceutica NV (BE)

( * ) Notice: Subject to any disclaimer, the term of this patent is extended or adjusted under 35 U.S.C. 154(b) by 1267 days.

(21) Appl. No.: 12/030,911

(22) Filed: Feb. 14, 2008

(65) Prior Publication Data

US 2008/0249122 A1 Oct. 9, 2008

Related U.S. Application Data

(60) Provisional application No. 60/910,678, filed on Apr. 9, 2007.

(51) Int. Cl.
*A61K 31/438* (2006.01)
*C07D 401/14* (2006.01)
*C07D 401/04* (2006.01)

(52) U.S. Cl.
USPC .......................................... 514/278; 546/18

(58) Field of Classification Search
USPC ........................................... 546/18; 514/278
See application file for complete search history.

(56) References Cited

U.S. PATENT DOCUMENTS

| | | | |
|---|---|---|---|
| 3,155,670 A | 11/1964 | Jan Janssen |
| 3,155,699 A | 11/1964 | Powers et al. |
| 3,161,644 A | 12/1964 | Janssen et al. |
| 3,238,216 A | 3/1966 | Adriaan |
| 3,629,267 A | 12/1971 | Kaiser et al. |
| 3,839,340 A | 10/1974 | Scharpf |
| 3,859,340 A | 1/1975 | Stiller et al. |
| 4,020,072 A | 4/1977 | Hoehn et al. |
| 4,233,307 A | 11/1980 | Ono et al. |
| 4,329,353 A | 5/1982 | Stokbroekx et al. |
| 4,414,216 A | 11/1983 | Kawakita et al. |
| 4,526,896 A | 7/1985 | Scherrer et al. |
| 5,486,362 A | 1/1996 | Kitchell et al. |
| 5,618,833 A | 4/1997 | Foulon et al. |
| 5,739,336 A | 4/1998 | Weinhardt et al. |
| 6,013,652 A | 1/2000 | Maccoss et al. |
| 6,043,366 A | 3/2000 | Adam et al. |
| 6,060,482 A | 5/2000 | Heine et al. |
| 6,071,925 A | 6/2000 | Adam et al. |
| 6,113,527 A | 9/2000 | Adam et al. |
| 6,172,076 B1 | 1/2001 | Embrey et al. |
| 6,262,066 B1 | 7/2001 | Tulshian et al. |
| 6,277,991 B1 | 8/2001 | Hohlweg et al. |
| 6,465,478 B1 | 10/2002 | Ito et al. |
| 6,777,421 B2 | 8/2004 | Jordan et al. |
| 7,053,101 B2 | 5/2006 | Jordan et al. |
| 7,081,463 B2 | 7/2006 | Battista et al. |
| 7,192,964 B2 | 3/2007 | Hashimoto et al. |
| 7,557,117 B2 | 7/2009 | Hashimoto et al. |
| 7,582,649 B2 | 9/2009 | Battista et al. |
| 7,655,670 B2 | 2/2010 | Battista et al. |
| 2001/0011092 A1 | 8/2001 | Tulshian et al. |
| 2003/0109538 A1 | 6/2003 | Carter et al. |
| 2003/0109539 A1 | 6/2003 | Jordan et al. |
| 2003/0158219 A1 | 8/2003 | Ito et al. |
| 2004/0014955 A1 | 1/2004 | Zamudio et al. |
| 2004/0142955 A1 | 7/2004 | Battista et al. |
| 2004/0152707 A1 | 8/2004 | Tulshian et al. |
| 2005/0004154 A1 | 1/2005 | Jordan et al. |
| 2005/0004363 A1 | 1/2005 | Hashimoto et al. |
| 2005/0038060 A1 | 2/2005 | Ando et al. |
| 2006/0079505 A1 | 4/2006 | Makings et al. |
| 2008/0200492 A1 | 8/2008 | Vaidya |

FOREIGN PATENT DOCUMENTS

| | | |
|---|---|---|
| EP | 0636609 | 2/1995 |
| EP | 0431943 | 7/1998 |
| EP | 08/56514 B1 | 8/1998 |
| EP | 0921125 B1 | 6/1999 |
| EP | 0997464 B1 | 2/2005 |
| JP | 2000-128879 | 5/2000 |
| JP | 2000-169476 | 6/2000 |
| WO | WO 88/00190 | 1/1988 |
| WO | WO 93/12789 | 7/1993 |
| WO | WO 95/07294 | 3/1995 |
| WO | WO 97/07212 | 2/1997 |
| WO | WO 97/07212 A1 | 2/1997 |
| WO | WO 97/36871 | 10/1997 |
| WO | WO 99/59997 | 11/1999 |
| WO | WO 99/65494 | 12/1999 |
| WO | WO 00/06545 | 2/2000 |
| WO | WO 00/06545 A1 | 2/2000 |
| WO | WO 0015222 | 3/2000 |
| WO | WO 00/31037 | 6/2000 |
| WO | WO 01/07050 A1 | 2/2001 |

(Continued)

OTHER PUBLICATIONS

What drugs are approved for Alzheimer Disease, Jul. 31, 2010. Fisher Center for Alzheimer Research Foundation.*
WichmannJurgen et al , 1999, 8-Acenapthen-1yl- 1-phenyl-1, 3, 8-Triaza-spiro[4, 5]decan-4-one derivatives as orphanin FQ receptor agonists.*
Wermuth Molecular Variation Based on Isosteric Replacement 1996.*
Avis, Kenneth E., Table of Contents, Pharmaceutical Dosage Forms, "Parenteral Medications", vols. 1 and 2.
Calo, Girolamo et al., "Pharmacology of nociceptin and its receptor: a novel therapeutic target", British Journal of Pharmacology, (2000), pp. 1261-1283, vol. 129.

(Continued)

*Primary Examiner* — Rita Desai
(74) *Attorney, Agent, or Firm* — Michele G. Mangini

(57) ABSTRACT

The present invention is directed to novel 1,3,8-trisubstituted-1,3,8-triaza-spiro[4.5]decan-4-one derivatives, pharmaceutical compositions containing them and their use in the treatment of disorders and conditions mediated by the ORL-1 G-protein coupled receptor.

34 Claims, No Drawings

(56) References Cited

FOREIGN PATENT DOCUMENTS

| WO | WO 01/36418 A1 | 5/2001 |
|---|---|---|
| WO | WO 01/38720 | 5/2001 |
| WO | WO 01/39723 A2 | 6/2001 |
| WO | WO 01/46192 | 6/2001 |
| WO | WO 01/46192 A1 | 6/2001 |
| WO | WO 01/94346 A1 | 12/2001 |
| WO | WO 01/96337 | 12/2001 |
| WO | WO 01/96337 A1 | 12/2001 |
| WO | WO 02/083673 A1 | 10/2002 |
| WO | WO 02/085355 A1 | 10/2002 |
| WO | WO 03/010168 A1 | 6/2003 |
| WO | WO 03/064425 | 8/2003 |
| WO | WO 03/066579 | 8/2003 |
| WO | WO 2004/022558 | 3/2004 |
| WO | WO 2004/022558 A | 3/2004 |
| WO | WO 2005/016913 | 2/2005 |
| WO | WO 2005/063745 | 7/2005 |
| WO | WO 2006/023852 | 3/2006 |
| WO | WO 2006/034015 | 3/2006 |
| WO | WO 2008/067177 | 6/2008 |
| WO | WO 2008/124209 | 10/2008 |
| WO | WO 2010/033451 | 3/2010 |

OTHER PUBLICATIONS

Haines, Duane E., "Federal of European Neuroscience Societies 2000 Meeting", News from the American Association of Anatomists, The Anatomical Record, pp. 261, vol. 48.

Lieberman, Herbert A., Table of Contents, "Pharmaceutical Dosage Forms—Disperse Systems" vols. 1-3.

Lieberman, Herbert A., Table of Contents, "Pharmaceutical Dosage Forms—Tablets", vols. 1-3.

Meunier, Jean-Claude et al., "Isolation and structure of the endogenous agonist of opioid receptor-like ORL1 receptor", Nature, Oct. 12, 1995, pp. 532-535, vol. 377.

Rowe, Raymond C. et al., Table of Contents, "Handbook of Pharmaceutical Excipients", Fifth Edition.

US Office Action U.S. Appl. No. 12/479,103, filed Aug. 30, 2011, OA Date Aug. 30, 2011.

US Office Action U.S. Appl. No. 11/939,789, filed Nov. 14, 2007, OA Date Jan. 10, 2012.

US Office Action U.S. Appl. No. 11/939,789, filed Nov. 14, 2007, OA Date Mar. 25, 2011.

EP Search Report, 08729 809.7-2101, Date Dec. 22, 2011.

PCT International Search Report, PCT/US2009/056796, dated May 4, 2010.

PCT International Search Report, PCT/US2008/080081, dated Jul. 17, 2008.

PCT International Search Report, PCT/US2007/084751, dated Aug. 25, 2008.

PCT International Search Report, PCT/US2007/084642, dated Mar. 26, 2008.

PCT International Search Report, PCT/US03/27956, dated Feb. 18, 2004.

U.S. Appl. No. 11/940,397, Office Action dated, Apr. 15, 2010.
U.S. Appl. No. 10/656,934, Office Action dated, Jul. 19, 2004.
U.S. Appl. No. 10/656,934, Office Action, dated Jul. 28, 2005.
U.S. Appl. No. 11/242,654, Office Action dated, May 29, 2008.
U.S. Appl. No. 11/242,654, Interview Summary dated, Jan. 3, 2009.
U.S. Appl. No. 11/398,239, Office Action dated, Mar. 20, 2009.
U.S. Appl. No. 10/909,858, Office Action dated Feb. 3, 2005.
U.S. Appl. No. 10/909,858, Office Action dated May 6, 2005.
U.S. Appl. No. 10/909,858, Office Action dated Jun. 14, 2005 Examiner Interview.
U.S. Appl. No. 11/939,789 Office Action dated May 29, 2012.
U.S. Appl. No. 11/940,397, Office Action Dated Oct. 4, 2011.
U.S. Appl. No. 11/398,239, Notice of Allowance and Notice of Allowability dated Jul. 20, 2012.
U.S. Appl. No. 11/398,239, Notice of Allowance and Notice of Allowability dated Mar. 1, 2011.
PCT/US02/10736 ISR, dated Jun. 27, 2002.
EP ISR Application No. 02 721 678.7-2117, dated Mar. 4, 2004.
U.S. Appl. No. 10/656,934, Office Action dated, Mar. 2, 2006.
U.S. Appl. No. 10/656,934, NOA, and Notice of Allowability Sep. 8, 2005.
U.S. Appl. No. 10/656,934, Office Action dated, Jan. 27, 2006.
U.S. Appl. No. 11/242,654, NOA dated, Jan. 16, 2009.
U.S. Appl. No. 11/242,654, NOA dated, May 11, 2009.
U.S. Appl. No. 11/242,654, Interview Summary, dated May 15, 2008.
U.S. Appl. No. 12//327,437, Office Action dated, May 28, 2009.
U.S. Appl. No. 12/327,437, Office Action dated, Aug. 26, 2009.
U.S. Appl. No. 12/327,437, filed Dec. 3, 2008.
U.S. Appl. No. 12/327,437, NOA and Notice of Allowability, dated, Jan. 5, 2010.
U.S. Appl. No. 12/327,437, NOA, and Notice of Allowability, dated May 6, 2010.
U.S. Appl. No. 11/398,239, NOA dated Sep. 28, 2010.
U.S. Appl. No. 11/398,239, filed, Apr. 5, 2006.
U.S. Appl. No. 11/939,789, filed, Nov. 14, 2007.
U.S. Appl. No. 11/939,789, Office Action dated Aug. 23, 2010.
U.S. Appl. No. 11/939,789, Office Action dated Oct. 21, 2010.
U.S. Appl. No. 11/940,397, filed Nov. 15, 2007.
U.S. Appl. No. 11/940,397, Office Action dated Oct. 29, 2010.
U.S. Appl. No. 11/940,397, Office Action dated Apr. 15, 2010.
U.S. Appl. No. 12/479,103, filed Jun. 5, 2009.
EP Search Report, Application No. 03 749 479.6-1521, dated Sep. 9, 2008.
U.S. Appl. No. 12/327,437, NOA and Notice of Allowability, May 6 2010.
U.S. Appl. No. 12/327,437, NOA and Notice of Allowability, Jan. 5, 2010.
U.S. Appl. No. 12/327,437, Office Action dated, Jan. 5, 2010 NOA.
U.S. Appl. No. 12/327,437, Office Action dated, May 6, 2010 NOA.
U.S. Appl. No. 10/909,858, Office Action dated Jun. 1, 2005.
U.S. Appl. No. 11/398,239, Office Action dated May 6, 2010.
U.S. Appl. No. 12/327,437 NOA, and Notice of Allowability, Jan. 10, 2012.
U.S. Appl. No. 12/327,437 NOA, and Notice of Allowability, Jan. 7, 2011.
U.S. Appl. No. 12/327,437 NOA, and Notice of Allowability, Sep. 7, 2010.

Bignan G.C., et al., "Recent Advanced Towards the Discovery of ORL-1 Receptor Agonists and Antagonists," 14(4) Expert Opinion. Ther. Patents 357-388 (2005).

Patani, et al, "Bioisosterism: A Rational Approach in Drug Design", Chem. R., 1996, pp. 3147-3176, vol. 96.

Cometta-Morini, et al., "Molecular Determinants of μ Receptor Recognition for the Fentanyl class of Compounds", Jan. 1992, pp. 185-196, vol. 41, No. 1.

Satyamurthy, et al., "3-(2'-[$^{18}$F]Fluoroethyl)spiperone, a Potent Dopamine Antagonist: Synthesis, Structural Analysis and In-vivo Utilization in Humans*", 1990, pp. 113-129, vol. 41, No. 2.

Wolf, et al, "Rational Development of Practical Catalysts for aromatic Carbon-Nitrogen Bond formation", Acc. Chem. Res., 1998, pp. 805-818, vol. 31.

Janssen C. STN English Abstract DN 60:90893 BE633914 Dec. 1963.

What drugs are approved for Alzheimer Disease, Jul. 31, 2010, Fisher Center for Alzheimer Research Foundation.

Kiesewetter, D. et al., "Syntheses and D.sub.2 Receptor Affinities of Derivatives of Spiperone Containing Aliphatic Halogens" Appl. Radiat. Isot., 1986, 37(12), 1181-1188.

Chalon, S. et al "Iodoethylspiperone, a New Potential Agent for Exploration of Central Dopamine D.sub.2 Receptors: Synthesis and Preliminary In Vivo Study" Nucl. Med. Bio. 1990, 17(4), 389-395.

Satyamurthy, N. et al., "3-(2'[.sup.18 F]Fluoroethyl)spiperone, a Potent Dopamine Antagonist: Synthesis, Structural Analysis and In-vivo Utilization in Humans" Appl. Radiat. Isot. 1990, 41(2), 113-129.

Meunier, Jean-Claude et al. "Isolation and structure of the endogenous agonist of opioid receptor-like ORL sub 1 receptor." Nature, 1995, 377, 532-535.

Rover S. et al., "High-Affinity, Non-Peptide Agonists for the ORL1 (Orphanin FQ/Nociceptin) Receptor" J. Med. Chem., 2000, 43, 1329-1338.

(56) References Cited

OTHER PUBLICATIONS

Jenck, Francois et al., "A synthetic agonist at the orphanin FQ/nociceptin receptor ORL1: Anxiolytic profile in the rat," *PNAS*, Apr. 25, 2000, vol. 97, No. 9, pp. 4938-4953.
Calo, Girolamo, et al., Pharmacology of nociceptin and its receptor: a novel therapeutic target. *Briti.J. of Pharm.* 2000, 129, 1261-1283.
Poulain, R. et al., "From Hit to Lead. Combining Two Complementary Methods for Focused Library Design. Application to .mu. Opiate Ligands" *J. Med. Chem.* 2001, 44, 3378-3390.
Poulain, R. et al., "From Hit to Lead. Analyzing Structure—Prof Relationship" *J.Med. Chem.* 2001, 44, 3391-3401.
Ronzoni, Silvano et al., "Lead generation and lead optimization approaches in the discovery of selective, non-peptide ORL-1 receptor agonists and antagonists," *Exp. Opin. Ther. Patents*, 2001, (11) 4, pp. 525-546.
Calo, G. et al., "Pharmacological Profile of Nociceptin/Orphanin FQ Receptors" *Clinical and Experimental Pharmacology and Physiology*; 2002, 29, 223-228.
Zaveri, Nurulain, "Peptide and nonpeptide ligands for the nociceptin/orphanin FQ receptor ORL1: Research tools and potential therapeutic agents," *Life Sciences* 73 2003, pp. 663-678.
Meunier, et al., "The potential therapeutic value of nociceptin receptor agonists and antagonists", Expect Opinion on Therapeutics Patents, 2000, pp. 371-388, vol. 10, (4).
Collier, et al., Br. J. Pharmacol., 1968, 32, 295.
Dirig, et al., J. Neurosci. Methods, 1997, 76, 183.
Dirig, et al., J. Pharmacol. Expt. Therap., 1998, 285, 1031.
Henderson G, et al., The orphan Opioid receptor and its endogenous ligandnociceptin/orphanin FQ:; Trends in Pharmacological Sciences, Elsevier Trends Journal, pp. 293-300, Aug. 1, 1997, vol. 18, No. 8, XP004085920; ISSN: 0165-6147, Cambridge, GB.
Higgins, et al., In European Forum of Neuroscience 2000, Brighton, U.K., Jun. 24-28, 2000, Poster 077.22.
Pellow et al., J. Neurosci Methods 14: 149-167, 1985.
Pulito, V.L. et al., 2000, J. Pharmacol. Exp. Ther. 294, 224-229.
Selway et al., Bioorganic & Medicinal vol. 4, No. 5 pp. 645-654 1996.
Thurkauf, A. et al., "1-Phenyl-3-(aminomethyl) pyrroles as Potential Antipsychotic Agents. Synthesis and Dopamine Receptor Binding", J. Med. Chem., 1995, pp. 4950-4952, vol. 38 No. 25.
Thurkauf, A., et al., 2-Phenyl-4-(aminomethyl) imidazoles as Potential Antipsychotic Agents. Synthesis and Dopamine D2 Receptor Binding:; J. Med. Chem.., 1995, pp. 2251-2255, vol. 38, No. 12, XP002203778.
Thurkauf, A. et al., "3-Aminomethylbiphenyls. A New Class of Dopamine Receptor Ligands", Med. Chem Res., 1996, pp. 69-80, vol. 6.
Whitney et al., J. Org. Chem. 1997, 62, 8962-8963.
Wolfe, et al., Tetrahedron, 1996, 52(21), 7525-7546.
Wolfe, J. et al., "Palladium-Catalyzed Amination of Aryl Triflates", J. Org. Chem. 1997, pp. 1264-1267, vol. 62, No. 5.
Yeager, et al., Synthesis, 1995, p. 28.
Greene, Theodora W. et al., "Protective Groups in Organic Synthesis", Table of Contents, John Wiley & Sons, 1991.
Haines, Duane E., "Federation of European Neuroscience Societies 2000 Meeting", News from the American Association of Anatomists, The Anatomical Record, pp. 261, vol. 48.
Kinouchi, Keiko et al., "Evidence for $k_1$ opioid receptor multiplicity in the guinea pig cerebellum" European Journal of Pharmacology—Molecular Pharmacology Section, (1991), pp. 135-141, vol. 207.
Lieberman, Herbert A. , Table of Contents, "Pharmaceutical Dosage Forms Disperse Systems" vols. 1-3. 1999.
Lieberman, Herbert A., Table of Contents, Pharmaceutical Dosage Forms Tablets:, vols. 1-3. 1992.
McOmie, J.F.W. et al., "Protective Groups in Organic Synthesis", Table of Contents, Plenum Press 1973.
Rowe, Raymond C. et al., Table of Contents, "Handbook of Pharmaceutical Excipients", Fifth Edition 2005.
Thomsen, Christian et al., "(8-Naphalen-1-ylmethyl-4-oxo-1-phenyl-1,3,8-triaza-spiro[4,5]-dec-3-yl)-acetic acid methyl ester (NNC 63/0532) is a novel potent nociceptin receptor agonist,"British Journal of Pharmacology (2000) 131, 903-908.
Randall, et al., "A Method for Measurement of Analgesic Activity on Inflamed Tissue ", Arch. Int. Pharmacodyn,1957, pp. 409-419, vol. 111 (4).
Jenck, et al., "A Synthetic Agonist at the Orphanin FQ/Nociceptin Receptor ORL1: Anxiolytic Profile in the Rat", PNAS, 2000, pp. 4938-4943, vol. 97 No. 9.
Rover, et al., "ORL1 Receptor Ligands: Structure-Activity Relationships of 8-Cycloalkyl-1-Phenyl-1,3,8-Triaza-Spiro[4.5]decan-4-ones", Biorganic & Medicinal Chemistry Letters, 2000, pp. 831-834, vol. 10.
Jordan, et al., "8-(Heteroaryl)Phenalkyl-1-Phenyl-1,3,8-Triazaspiro[4.5]Decan-4-ones Opioid as Receptor Modulators" Medicinal Chemistry, 2005, pp. 601-610, vol. 1.
Bignan, et al., "Recent Advances Towards the Discovery of ORL-1 Receptor Agonists and Antagonists" Expert Opinion, 2005, pp. 357-388, vol. 15 (4).
Wang, et al., "cDNA Cloning of an Orphan Opiate Receptor Gene Family Member and Its Splice Variant", FEBS Letters, 1994, pp. 75-79, vol. 348.
Chen, et al., "Molecular Cloning, Tissue Distribution and Chromosomal Localization of a Novel Member of the Opiod Receptor Gene Family", FEBS Letters, 1994, pp. 279-283, vol. 347.
Fukuda, et al., "cDNA Cloning and Regional Distribution of a Novel Member of the Opioid Receptor Family", FEBS Letters, 1994, pp. 42-46, vol. 343.
Bunzow, et al., "Molecular Cloning and Tissue Distribution of a Putative Member of the rat Opioid Receptor Gene family That Is Not a μ, S or k Opioid Receptor Type", FEBS Letters, 1994, pp. 284-288, vol. 347.
Ross, et al., "Aminopyrimidines as Neuroprotective Agents" American Chemical Society, Abstracts of Papers, $230^{th}$ ACS National Meeting, Washington, DC United States, Aug. , Sep. 1, 2005, MEDI-039. AN 2005: 739554 CAPLUS.
Bröer, "Molecular Modelling Studies on the ORL1-Receptor and ORL1-Agonists", Journal of Computer-Aided Molecular Design, 2003, pp. 739-754, vol. 17.
Abdel-Magid, "Reductive Amination of Aldehydes and Ketones with Sodium Triacetoxyborohydride. Studies on Direct and Indirect Reductive Amination Procedures", J. Org. Chem., 1996, pp. 3849-3862, vol. 61.
Wichmann, "8-Acenaphthen-1-YI-1-Phenyl-1,3,8-Triaza-Spiro[4.5]Decan-4-One Derivatives As Orphanin FQ Receptor Agonists", Bioorganic & Medicinal Chemistry Letters, 1999, pp. 2343-2348, vol. 9.
Calo, Pharmacology of Nociceptin and Its Receptor: a Novel Therapeutic Target, 2000, pp. 1261-1283, vol. 129.
Lambert, "The nociceptin/orphanin FQ receptor: a target with broad therapeutics potential" Nature Reviews, Aug. 2008, pp. 694-710, vol. 7.
Bignan, et al., "Recent Advanced Towards the Discovery of ORL-1 Receptor Agonists and Antagonists," 14(4) Expert Opinion. Ther. Patents 357-388 (2005).
Zaveri, "Peptide and Nonpeptide Ligands for the Nociceptin/Orphanin FQ Receptor ORL 1: Research Tools and Potential Therapeutic Agents," 73 Life Sciences 663-678 (2003).
Koster, et al., "Combined Pharmacological and Genetic Approach to Studying the Role of Orphanin FQ on Cognition" PNAS, pp. 10444-10449, vol. 96. 1999.
Acsàdy, L., et. al., "Nerve Growth Factor But Not Neurotrophin-3 Is Synthesized by Hippocampal Gabaergic Neurons That Project to the Medial Septum." *Neuroscience*, vol. 98, No. 1, pp. 23-31. 2000.
Avis, Kenneth E., Table of Contents, Pharmaceutical Dosage Forms, "Parenteral Medications", vols. 1 and 2. 1991.
Chung, et al., "Therapy for Cough: Active Agents", Pulmonary Pharmacology & Therapeutics, 2002, pp. 335-338, vol. 15.
Groneberg,et al., "Endogenous Opioids as Mediators of Asthma", Pulmonary Pharmacology & Therapeutics, 2001, pp. 383-389, vol. 14.
Wermuth, et al, The Latest Chemistry of Drug Discovery, last volume, Technomics, Inc. 1999, 9. 25 pages 347 to 349, 359, 360, 452 and 453.

(56) References Cited

OTHER PUBLICATIONS

Okano, General Theory of New Pharmacology (Revised Third edition), Nankodo Co., Led., 1987, 4, 10 pages 26, 111, 256 and 257.

Meuiner, J. et al., "Isolation and Structure of the Endogenous Agonist of Opioid Receptor-Like $ORL_1$ Receptor", Nature, Oct. 12, 1995, pp. 532-535, vol. 377.

Ciccocioppo, et al., "Effect of nociceptin on alcohol intake in alcohol-preferring rats", Psychopharmacology, 1999, pp. 220-224, vol. 141.

Ciccocioppo, et al., "The nociceptin/orphanin FQ/NOP receptor system as a target for treatment of alcohol abuse: a review of recent work in alcohol-preferring rats", Physiology & Behavior, 2003, pp. 121-128, vol. 79.

Polidori, et al., "Pharmacological characterization of the nociceptin receptor mediating hyperphagia: identification of a selective antagonist", Psychopharmacology, 2000, pp. 430-437, vol. 148.

Wise, et al., "Examination of a Series of 8-[3-[Bis(4-fluorophenyl)amino]propyl]-1-aryl-1,3,8-triazaspiro[4.5]decan-4-ones as Potential Antipsychotic Agents", J. Med. Chem. 1985, pp. 1811-1817, vol. 28.

Rizzi, et al., "Nociceptin Receptor Activation Inhibits Tachykinergic Non Adrenergic Non Cholinergic Contraction of Guinea Pig Isolated Bronchus", 1999, vol. 64, No. 13, pp. 157-163.

Redrobe, et al., "Nociceptin Receptor Antagonists Display antidepressant-Like Properties in the Mouse forced Swimming Test", Naunyn-Schmiedeberg's Arch Pharmacol, 2002, vol. 365, pp. 164-167.

U.S. Appl. No. 12/327,437, filed Dec. 3, 2008, Notice of Allowance, Date Jul. 10, 2013.

U.S. Appl. No. 12/327,437, filed Dec. 3, 2008, Notice of Allowance, Date Apr. 3, 2013.

U.S. Appl. No. 12/327,437, filed Dec. 3, 2008, Notice of Allowance, Date May 14, 2012.

U.S. Appl. No. 12/327,437, filed Dec. 3, 2008, Notice of Allowance, Date Sep. 6, 2010.

U.S. Appl. No. 11/939,789, filed Nov. 14, 2007, Examiner initiated Interview Summary, Date Jul. 15, 2013.

U.S. Appl. No. 11/939,789, filed Nov. 14, 2007, Office Action, Date Mar. 1, 2013.

U.S. Appl. No. 11/939,789, filed Nov. 14, 2007, Examiner initiated Interview Summary, Date Jan. 7, 2013.

U.S. Appl. No. 11/939,789, filed Nov. 14, 2007, Final Office Action, Date May 29, 2012.

U.S. Appl. No. 12/327,437, Notice of Allowance, Dated Oct. 29, 2013.

U.S. Appl. No. 11/939,789, filed Nov. 14, 2007, Notice of Allowance Date Jul. 23, 2013.

U.S. Appl. No. 11/939,789, filed Nov. 14, 2007, Notice of Allowance, Date Jul. 24, 2013.

U.S. Appl. No. 11/939,789, filed Nov. 14, 2007, Examiner Initiated Interview Summary, Date Jun. 21, 2013.

U.S. Appl. No. 11/939,789, filed Nov. 14, 2007, Office Action, Date Apr. 16, 2013.

U.S. Appl. No. 11/440,731, filed May 25, 2006, OA Date Mar. 11, 2009.

U.S. Appl. No. 11/440,731, filed May 25, 2006, OA Date May 20, 2009.

U.S. Appl. No. 11/440,731, filed May 25, 2006, NOA and Examiner's Interview, Date, Sep. 18, 2010.

U.S. Appl. No. 11/440,731, filed May 25, 2006, OA Date Nov. 23, 2009.

ISR PCT/US06/20211, Date Sep. 26, 2007.

EP Search Report, Date Apr. 6, 2010, EP06771149.

Response to EP Search Report, Date Dec. 3, 2010.

Haynes, et al. "Stereoselective, Base-Induced Formation of bicycle [2.2.1] Heptanones and Bicyclo [3.2.1.] Octanols Formed from the Products of Conjugation Addition of Lithiated Allylic Sulfoxides and Phosphine Oxides to Cyclopen-2-enone." Australian Journal of Chemistry, Sep. 1989, vol. 42, No. 9, pp. 1473-1483, p. 1473, abstract.

\* cited by examiner

US 8,741,916 B2

1,3,8-TRISUBSTITUTED-1,3,8-TRIAZA-SPIRO [4.5]DECAN-4-ONE DERIVATIVES AS LIGANDS OF THE ORL-1 RECEPTOR

CROSS REFERENCE TO RELATED APPLICATIONS

This application claims the benefit of U.S. Provisional Application 60/910,678, filed on Apr. 9, 2007, which is incorporated by reference herein in its entirety.

FIELD OF THE INVENTION

The present invention is directed to novel 1,3,8-trisubstituted-1,3,8-triaza-spiro[4.5]decan-4-one derivatives, pharmaceutical compositions containing them and their use in the treatment of disorders and conditions mediated by the ORL-1 G-protein coupled receptor. More particularly, the compounds of the present invention are useful in the treatment of disorders and conditions such as anxiety, depression, panic, mania, dementia, bipolar disorder, substance abuse, neuropathic pain, acute pain, chronic pain, migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorder (ADHD), Alzheimer's disease, for improved cognition or memory and for mood stabilization.

BACKGROUND OF THE INVENTION

The ORL-1 (orphan opioid receptor) G-protein coupled receptor, also known as the nociceptin receptor, was first reported in 1994, and was discovered based on its homology with the classic delta-(OP-1), mu-(OP-3), and kappa-(OP-2) opioid receptors. The ORL-1 G-protein coupled receptor does not bind opioid ligands with high affinity. The amino acid sequence of ORL-1 is 47% identical to the opioid receptors overall, and 64% identical in the transmembrane domains. (*Nature*, 1995, 377, 532.)

The endogenous ligand of ORL-1, known as nociceptin, a highly basic 17 amino acid peptide, was isolated from tissue extracts in 1995. It was named both nociceptin, because it increased sensitivity to pain when injected into mouse brain, and orphanin FQ (OFQ) because of the terminal phenylalanine (F) and glutamine (Q) residues that flank the peptide on the N- and C-termini respectively. (WO97/07212)

Nociceptin binding to ORL-1 receptors causes inhibition of cAMP synthesis, inhibition of voltage-gated calcium channels, and activation of potassium conductance. In vivo, nociceptin produces a variety of pharmacological effects that at times oppose those of the opioids, including hyperalgesia and inhibition of morphine-induced analgesia. Mutant mice lacking nociceptin receptors show better performance in learning and memory tasks. These mutant mice also have normal responses to painful stimuli.

The ORL-1 receptor is widely distributed/expressed throughout the human body, including in the brain and spinal cord. In the spinal cord, the ORL-1 receptor exists in both the dorsal and ventral horns, and precursor mRNA has been found in the superficial lamina of the dorsal horn, where primary afferent fibers of nociceptors terminate. Therefore, the ORL-1 has an important role in nociception transmission in the spinal cord. This was confirmed in recent studies wherein nociceptin, when given to mice by i.c.v. injection, induced hyperalgesia and decreased locomotor activity. (*Brit. J. Pharmacol.* 2000, 129, 1261.)

Ito, et al., in EP 0997464 disclose 1,3,8-triazaspiro[4.5]decan-4-one compounds as ORL-1 receptor agonists, useful as analgesics or the like in mammalian subjects.

Hohlweg et al., in PCT publication WO 01/36418 disclose triazaspirodecanones with high affinity for opioid receptor subtypes useful in the treatment of migraine, non-insulin dependent diabetes mellitus, sepsis, inflammation, incontinence and/or vasomotor disturbances.

Tulshian et al. in PCT publication WO0/06545 disclose high affinity ligands for the nociceptin receptor ORL-1 and the use of said compounds as nociceptin receptor inhibitors useful in the treatment of pain, anxiety, cough, asthma, depression and alcohol abuse.

Higgins, et. al., in European Forum of Neuroscience 2000, Brighton, U.K., Jun. 24-28, 2000, Poster 077.22 disclosed, 8-[(1R,3aS)-2,3,3a,4,5,6-hexahydro-1H-phenalen-1-yl]-1-phenyl-1,3,8-triazaspiro[4.5]decan-4-one useful as cognition enhancers.

Jordan et al., in United States Patent Publication US-2003-0109538-A1, published Jun. 12, 2003 disclose 1,3,8-triazaspiro[4.5]decan-4-one derivatives useful in the treatment of disorders and conditions mediated by the ORL-1 G-protein coupled receptor.

Battista et al., in United States Patent Publication US-2004-0142955-A1, published Jul. 22, 2004 disclose 1,3,8-triazaspiro[4.5]decan-4-one derivatives useful in the treatment of disorders and conditions mediated by the ORL-1 G-protein coupled receptor.

We now describe novel small molecule modulators of the ORL-1 receptor, useful for the treatment of disorders and conditions mediated by the ORL-1 receptor, such as anxiety, depression, panic, dementia, mania, bipolar disorder, substance abuse, neuropathic pain, acute pain, chronic pain, migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorders (ADHD), Alzheimer's disease, for improved cognition or memory and for mood stabilization.

SUMMARY OF THE INVENTION

The present invention is directed to compounds of formula (I)

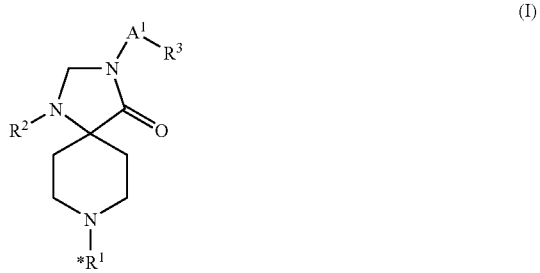

wherein
$R^1$ is 1-acenaphthenyl;
$R^2$ is 4-fluorophenyl;
$A^1$ is selected from the group consisting of —$CH_2$—, —$CH_2CH_2$—, —$CH_2CH_2CH_2$— and —$CH_2CH_2CH_2CH_2$—;

$R^3$ is selected from the group consisting of

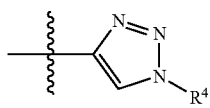

and

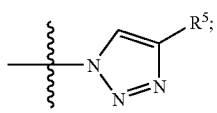

wherein $R^4$ is selected from the group consisting of hydroxy, cycloalkyl, phenyl, benzyl, imidazolyl, pyridyl, —$C_{1-4}$alkyl-$NR^AR^B$, —$C_{1-4}$alkyl-OH, —$C_{1-4}$alkyl-O—$C_{1-4}$alkyl, —C(O)OH and —C(O)O—$C_{1-4}$alkyl;

wherein the phenyl, imidazolyl or pyridyl, is optionally substituted with one or more (preferably one to two more preferably one) substituents independently selected from the group consisting of halogen and $C_{1-4}$alkyl;

wherein $R^A$ and $R^B$ are each independently selected from the group consisting of hydrogen and $C_{1-4}$alkyl;

and wherein $R^5$ is selected from the group consisting of hydroxy, cycloalkyl, phenyl, benzyl, imidazolyl, pyridyl, —$C_{1-4}$alkyl-$NR^CR^D$, —$C_{1-4}$alkyl-OH, —$C_{1-4}$alkyl-O—$C_{1-4}$alkyl, —C(O)OH and —C(O)O—$C_{1-4}$alkyl;

wherein the phenyl, imidazolyl or pyridyl, is optionally substituted with one or more (preferably one to two more preferably one) substituents independently selected from the group consisting of halogen and $C_{1-4}$alkyl;

and wherein $R^C$ and $R^D$ are each independently selected from the group consisting of hydrogen and $C_{1-4}$alkyl;

and pharmaceutically acceptable salts thereof.

The present invention is further directed to compounds of formula (II)

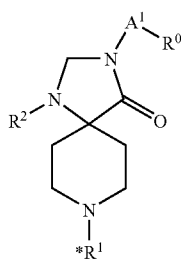

(II)

wherein
$R^1$ is 1-acenaphthenyl;
$R^2$ is 4-fluorophenyl;
$A^1$ is selected from the group consisting of —$CH_2$—, —$CH_2CH_2$—, —$CH_2CH_2CH_2$— and —$CH_2CH_2CH_2CH_2$—;
$R^0$ is selected from the group consisting of —CCH, hydroxy, —$N_3$, —O—C(O)—$C_{1-4}$alkyl, —O—$SO_2$—$C_{1-4}$alkyl, —O-(2-tetrahydropyranyl);

and pharmaceutically acceptable salts thereof. The compounds of formula (II) are intermediates in the synthesis of the compounds of formula (I).

Present invention is further directed to processes for the preparation of the compounds of formula (I) or compound of formula (II) and pharmaceutically acceptable salts thereof. The present invention is further directed to a product prepared according to any of the processes described herein.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating disorders and conditions mediated by the ORL-1 receptor in a subject in need thereof comprising administering to the subject a therapeutically effective amount of any of the compounds or pharmaceutical compositions described above.

An example of the invention is a method of treating a condition selected from the group consisting of anxiety, depression, panic, mania, dementia, bipolar disorder, substance abuse, neuropathic pain, acute pain, chronic pain, migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorder (ADHD), Alzheimer's disease, for improved cognition or memory and for mood stabilization, in a subject in need thereof comprising administering to the subject a therapeutically effective amount of any of the compounds or pharmaceutical compositions described above.

Another example of the invention is the use of any of the compounds described herein in the preparation of a medicament for treating: (a) anxiety, (b) depression, (c) panic, (d) mania, (e) dementia, (f) bipolar disorder, (g) substance abuse (h) neuropathic pain, (i) acute pain, (j) chronic pain, (k) migraine, (l) asthma, (m) cough, (n) psychosis, (o) schizophrenia, (p) epilepsy, (q) hypertension, (r) obesity, (s) eating disorders, (t) cravings, (u) diabetes, (v) cardiac arrhythmia, (w) irritable bowel syndrome, (x) Crohn's disease, (uy) urinary incontinence, (z) adrenal disorders, (aa) attention deficit disorder (ADD), (bb) attention deficit hyperactivity disorder (ADHD), (cc) Alzheimer's disease, for (dd) improved cognition, (ee) improved memory and (ff) mood stabilization, in a subject in need thereof.

DETAILED DESCRIPTION OF THE INVENTION

The present invention is directed to compounds of formula (I)

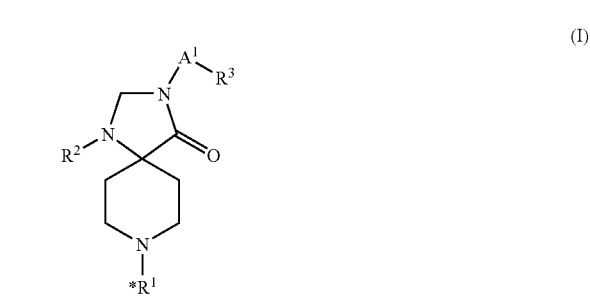

(I)

wherein $R^1$, $R^2$, $A^1$ and $R^3$ are as herein defined, and pharmaceutically acceptable salts thereof. The compounds of formula (I) are useful in the treatment of disorders mediated by the ORL-1 receptor. More particularly, the compound of formula (I) are useful in the treatment of anxiety, depression, panic, mania, dementia, bipolar disorder, substance abuse, neuropathic pain, acute pain, chronic pain migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorder (ADHD), Alzheimer's disease, for improved cognition or memory and for mood stabilization. Preferably, the compounds of formula (I) are useful in the treatment of anxiety, depression, substance abuse, neuropathic pain, acute pain, chronic pain, migraine, cough, hypertension, cardiac arrhythmia, irritable bowel syndrome and Crohn's disease. More preferably, the compounds of formula (I) are useful the treatment of anxiety, depression, neuropathic pain, acute pain, chronic pain and migraine.

The present invention is further directed to compounds of formula (II),

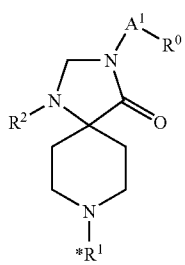

(II)

wherein $R^1$, $R^2$, $A^1$ and $R^0$ are as herein defined, and pharmaceutically acceptable salts thereof. The compounds of formula (II) are useful as intermediates in the synthesis of the compounds of formula (I). The compounds of formula (II) are further useful in the treatment of disorders mediated by the ORL-1 receptor. More particularly, the compound of formula (II) are useful in the treatment of anxiety, depression, panic, mania, dementia, bipolar disorder, substance abuse, neuropathic pain, acute pain, chronic pain migraine, asthma, cough, psychosis, schizophrenia, epilepsy, hypertension, obesity, eating disorders, cravings, diabetes, cardiac arrhythmia, irritable bowel syndrome, Crohn's disease, urinary incontinence, adrenal disorders, attention deficit disorder (ADD), attention deficit hyperactivity disorder (ADHD), Alzheimer's disease, for improved cognition or memory and for mood stabilization. Preferably, the compounds of formula (II) are useful in the treatment of anxiety, depression, substance abuse, neuropathic pain, acute pain, chronic pain, migraine, cough, hypertension, cardiac arrhythmia, irritable bowel syndrome and Crohn's disease. More preferably, the compounds of formula (II) are useful the treatment of anxiety, depression, neuropathic pain, acute pain, chronic pain and migraine.

In an embodiment of the present invention, the stereocenter as denoted by the "*" symbol in the compound of formula (I) below

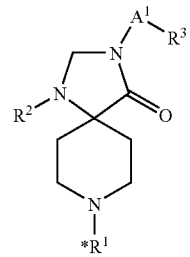

(I)

is present in the S-stereo-configuration. In another embodiment of the present invention, the stereocenter as denoted by the "*" symbol in the compound of formula (I) is present in the R-stereo-configuration. In another embodiment of the present invention, the compound of formula (I) is present as a racemate. In another embodiment of the present invention, the compound of formula (I) is present in an enantiomeric excess of about 80%, more preferably, in an enantiomeric excess of to about 90%, more preferably still, in an enantiomeric excess of about 95%, more preferably still, in an enantiomeric excess of about 98%, most preferably, at an enantiomeric excess about 99%.

In an embodiment, the present invention is directed to compounds of formula (Ia)

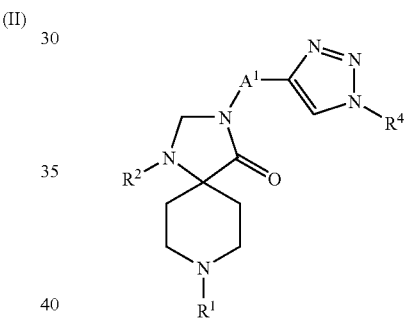

(Ia)

wherein $R^1$, $R^2$, $A^1$ and $R^4$ are as herein defined, and pharmaceutically acceptable salts thereof. In another embodiment, the present invention is directed to compounds of formula (Ib)

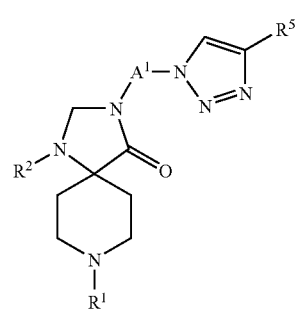

(Ib)

wherein $R^1$, $R^2$, $A^1$ and $R^5$ are as herein defined, and a pharmaceutically acceptable salts thereof.

In an embodiment of the present invention, $A^1$ is selected from the group consisting of —$CH_2CH_2$—, —$CH_2CH_2CH_2$— and —$CH_2CH_2CH_2CH_2$—. In another embodiment of the present invention, $A^1$ is selected from the group consisting of —CH₂CH₂— and —CH₂CH₂CH₂—. In another embodiment of the present invention, A¹ is —CH₂CH₂—. In another embodiment of the present invention, A¹ is —CH₂CH₂CH₂—.

In an embodiment of the present invention, R³ is selected from the group consisting of

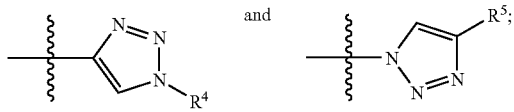

wherein R⁴ is selected from the group consisting of hydroxy, C₃₋₈cycloalkyl, phenyl, benzyl, imidazolyl, pyridyl, —C₁₋₄alkyl-NRᴬRᴮ, —C₁₋₄alkyl-OH, —C₁₋₄alkyl-O—C₁₋₄alkyl, and —C(O)O—C₁₋₄alkyl; wherein the phenyl, imidazolyl or pyridyl, is optionally substituted with one to two substituents independently selected from the group consisting of halogen and C₁₋₄alkyl; and wherein Rᴬ and Rᴮ are each independently selected from the group consisting of hydrogen and C₁₋₄alkyl; and wherein R⁵ is selected from the group consisting of hydroxy, C₃₋₈cycloalkyl, phenyl, benzyl, imidazolyl, pyridyl, —C₁₋₄alkyl-NRᶜRᴰ, —C₁₋₄alkyl-OH, —C₁₋₄alkyl-O—C₁₋₄alkyl, and —C(O)O—C₁₋₄alkyl; wherein the phenyl, imidazolyl or pyridyl, is optionally substituted with one to two substituents independently selected from the group consisting of halogen and C₁₋₄alkyl; and wherein Rᶜ and Rᴰ are each independently selected from the group consisting of hydrogen and C₁₋₄alkyl.

In another embodiment of the present invention, R³ is selected from the group consisting of

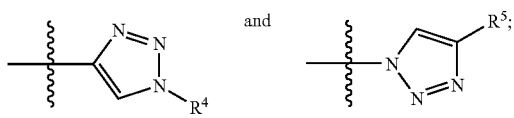

wherein R⁴ is selected from the group consisting of hydroxy, C₃₋₈cycloalkyl, phenyl, benzyl, imidazolyl, pyridyl, —C₁₋₂alkyl-NRᴬRᴮ, —C₁₋₂alkyl-OH, —C₁₋₂alkyl-O—C₁₋₂alkyl and —C(O)O—C₁₋₂alkyl; wherein the phenyl or imidazolyl is optionally substituted with substituent selected from the group consisting of halogen and C₁₋₂alkyl; and wherein Rᴬ and Rᴮ are each independently selected from the group consisting of hydrogen and C₁₋₂alkyl and wherein R⁵ is selected from the group consisting of hydroxy, C₃₋₈cycloalkyl, phenyl, benzyl, imidazolyl, pyridyl, —C₁₋₂alkyl-NRᴬRᴮ, —C₁₋₂alkyl-OH, —C₁₋₂alkyl-O—C₁₋₂alkyl and —C(O)O—C₁₋₂alkyl; wherein the phenyl or imidazolyl is optionally substituted with substituent selected from the group consisting of halogen and C₁₋₂alkyl; and wherein Rᶜ and Rᴰ are each independently selected from the group consisting of hydrogen and C₁₋₂alkyl.

In another embodiment of the present invention, R³ is selected from the group consisting of 4-(1-benzyl-1,2,3-triazolyl), 1-(4-(methylaminomethyl-1,2,3-triazolyl), 1-(4-hy-droxy-1,2,3-triazolyl), 1-(4-cyclopropyl-1,2,3-triazolyl), 1-(4-(methoxymethyl)-1,2,3-triazolyl), 1-(4-(dimethylaminomethyl)-1,2,3-triazolyl), 1-(4-(3-fluorophenyl)-1,2,3-triazolyl), 1-(4-(hydroxymethyl)-1,2,3-triazolyl), 1-(4-(ethoxycarbonyl)-1,2,3-triazolyl), 1-(4-(2-(1-methyl-imidazolyl))-1,2,3-triazolyl) and 1-(4-(3-pyridyl)-1,2,3-triazolyl).

In an embodiment of the present invention, R³ is 4-(1-benzyl-1,2,3-triazolyl). In another embodiment of the present invention, R³ is selected from the group consisting of 1-(4-(methylaminomethyl-1,2,3-triazolyl), 1-(4-hydroxy-1,2,3-triazolyl), 1-(4-cyclopropyl-1,2,3-triazolyl), 1-(4-(methoxymethyl)-1,2,3-triazolyl), 1-(4-(dimethylaminomethyl)-1,2,3-triazolyl), 1-(4-(3-fluorophenyl)-1,2,3-triazolyl), 1-(4-(hydroxymethyl)-1,2,3-triazolyl), 1-(4-(ethoxycarbonyl)-1,2,3-triazolyl), 1-(4-(2-(1-methyl-imidazolyl))-1,2,3-triazolyl) and 1-(4-(3-pyridyl)-1,2,3-triazolyl).

In another embodiment of the present invention, R³ is selected from the group consisting of 1-(4-(methylaminomethyl-1,2,3-triazolyl), 1-(4-hydroxy-1,2,3-triazolyl), 1-(4-cyclopropyl-1,2,3-triazolyl), 1-(4-(methoxymethyl)-1,2,3-triazolyl), 1-(4-(dimethylaminomethyl)-1,2,3-triazolyl), 1-(4-(3-fluorophenyl)-1,2,3-triazolyl), 1-(4-(hydroxymethyl)-1,2,3-triazolyl), 1-(4-(2-(1-methyl-imidazolyl))-1,2, 3-triazolyl) and 1-(4-(3-pyridyl)-1,2,3-triazolyl). In another embodiment of the present invention, R³ is selected from the group consisting of 1-(4-(methylaminomethyl-1,2,3-triazolyl), 1-(4-hydroxy-1,2,3-triazolyl), 1-(4-(methoxymethyl)-1,2,3-triazolyl), 1-(4-(dimethylaminomethyl)-1,2,3-triazolyl) and 1-(4-(3-fluorophenyl)-1,2,3-triazolyl). In another embodiment of the present invention, R³ is selected from the group consisting of 1-(4-(methylaminomethyl-1,2,3-triazolyl) and 1-(4-(methoxymethyl)-1,2,3-triazolyl).

In an embodiment of the present invention, R⁰ is selected from the group consisting of —CCH, hydroxy, —N₃, —O—C(O)—C₁₋₂alkyl, —O—SO₂—C₁₋₂alkyl and —O-(2-tetrahydropyranyl). In another embodiment of the present invention, R⁰ is selected from the group consisting of —CCH, —OH, —N₃, —O—C(O)—CH₃, —O—SO₂—CH₃ and —O-(2-tetrahydrodpyranyl). In another embodiment of the present invention, R⁰ is selected from the group consisting of —OH, —N₃, —O—C(O)—CH₃ and —O-(2-tetrahydrodpyranyl). In another embodiment of the present invention, R⁰ is —OH.

Additional embodiments of the present invention, include those wherein the substituents selected for one or more of the variables defined herein (i.e. R¹, R², A¹, R³, R⁴ and R⁵ are independently selected to be any individual substituent or any subset of substituents selected from the complete list as defined herein.

In another embodiment of the present invention is any single compound or subset of compounds selected from the representative compounds listed in Table 1, below.

Representative compounds of the present invention are as listed in Table 1 below. Unless otherwise noted, wherein a stereogenic center is present in the listed compound, as denoted by the (*) in the structure at the top of the table, the compound was prepared as a mixture of stereo-configurations. Wherein the compound was prepared with one stereoisomer in excess, the S and R designations are intended to indicate which stereoisomer was prepared in enantiomeric excess. Unless otherwise indicated, the exact stereo-configuration (e.g. the optical rotation) of the center has not been determined.

TABLE 1

Representative Compounds of Formula (I)

| ID No. | Stereo (*) | A¹ | R³ |
|---|---|---|---|
| 8 | S | —CH₂CH₂— | 4-(1-benzyl-1,2,3-triazolyl) |
| 20 | R | —CH₂CH₂— | 1-(4-(methyl-amino-methyl)-1,2,3-triazolyl) |
| 21 | S | —CH₂CH₂— | 1-(4-(methyl-amino-methyl)-1,2,3-triazolyl) |
| 22 | R | —CH₂CH₂— | 1-(4-hydroxy-1,2,3-triazolyl) |
| 23 | S | —CH₂CH₂— | 1-(4-hydroxy-1,2,3-triazolyl) |
| 24 | R | —CH₂CH₂— | 1-(4-cyclopropyl-1,2,3-triazolyl) |
| 25 | S | —CH₂CH₂— | 1-(4-cyclopropyl-1,2,3-triazolyl) |
| 26 | R | —CH₂CH₂— | 1-(4-(methoxy-methyl)-1,2,3-triazolyl) |
| 27 | S | —CH₂CH₂— | 1-(4-(methoxy-methyl)-1,2,3-triazolyl) |
| 28 | R | —CH₂CH₂— | 1-(4-(dimethyl-amino-methyl)-1,2,3-triazolyl) |
| 29 | S | —CH₂CH₂— | 1-(4-(dimethyl-amino-methyl)-1,2,3-triazolyl |
| 30 | S | —CH₂CH₂CH₂— | 1-(4-(3-fluoro-phenyl)-1,2,3-triazolyl) |
| 31 | R | —CH₂CH₂CH₂— | 1-(4-(3-fluoro-phenyl)-1,2,3-triazolyl) |
| 32 | S | —CH₂CH₂CH₂— | 1-(4-(hydroxy-methyl)-1,2,3-triazolyl) |
| 33 | R | —CH₂CH₂CH₂— | 1-(4-(hydroxy-methyl)-1,2,3-triazolyl) |
| 34 | S | —CH₂CH₂CH₂— | 1-(4-(methyl-amino-methyl)-1,2,3-triazolyl) |
| 35 | R | —CH₂CH₂CH₂— | 1-(4-(methyl-amino-methyl)-1,2,3-triazolyl) |
| 36 | S | —CH₂CH₂CH₂— | 1-(4-(ethoxy-carbonyl)-1,2,3-triazolyl) |
| 37 | R | —CH₂CH₂CH₂— | 1-(4-(ethoxy-carbonyl)-1,2,3-triazolyl) |
| 38 | R | —CH₂CH₂— | 1-(4-(5-(1-methyl-imidazolyl))-1,2,3-triazolyl) |
| 39 | S | —CH₂CH₂— | 1-(4-(5-(1-methyl-imidazolyl))-1,2,3-triazolyl) |
| 40 | R | —CH₂CH₂— | 1-(4-(3-pyridyl)-1,2,3-triazolyl) |
| 41 | S | —CH₂CH₂— | 1-(4-(3-pyridyl)-1,2,3-triazolyl) |

Representative compounds of formula (II), intermediates in the synthesis of the compounds of formula (I) are as listed in Table 2 below.

TABLE 2

Representative Compounds of Formula (II)

| ID No. | Stereo (*) | A¹ | R⁰ |
|---|---|---|---|
| 1 | S | —CH₂CH₂— | —CCH |
| 9 | R | —CH₂CH₂— | —OH |
| 10 | S | —CH₂CH₂— | —O—SO₂—CH₃ |
| 11 | R | —CH₂CH₂— | —O—SO₂—CH₃ |
| 12 | S | —CH₂CH₂— | —O—C(O)—CH₃ |
| 13 | S | —CH₂CH₂— | —OH |
| 14 | S | —CH₂CH₂CH₂— | —N₃ |
| 15 | S | —CH₂CH₂CH₂— | —O-(2-tetrahydropyranyl) |
| 16 | R | —CH₂CH₂CH₂— | —N₃ |
| 17 | R | —CH₂CH₂— | —O-(2-tetrahydropyranyl) |
| 18 | S | —CH₂CH₂— | —N₃ |
| 19 | R | —CH₂CH₂— | —N₃ |

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{1-4}$" when used with alkyl means a carbon chain composition of 1-4 carbon atoms.

As used herein, unless otherwise noted, the term "cycloalkyl" shall mean any stable 3-8 membered monocyclic, saturated ring system, for example cyclopropyl, cyclobutyl, cyclopentyl, cyclohexyl, cycloheptyl and cyclooctyl.

When a particular group is "substituted" (e.g., alkyl, cycloalkyl, aryl, heteroaryl, heterocycloalkyl, etc.), that group may have one or more substituents, preferably from one to five substituents, more preferably from one to three substituents, most preferably from one to two substituents, independently selected from the list of substituents.

With reference to substituents, the term "independently" means that when more than one of such substituents is possible, such substituents may be the same or different from each other.

As used herein, the notation "*" shall denote the presence of a stereogenic center.

As used herein, unless otherwise noted, the term "isolated form" shall mean that the compound is present in a form which is separate from any solid mixture with another compound(s), solvent system or biological environment.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

One skilled in the art will further recognize that in the compounds of formula (I), wherein the compound is present in a mixture of about equal amounts of both enantiomers at the "*" position, then the compound is said to be present as a racemate or a racemic mixture.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

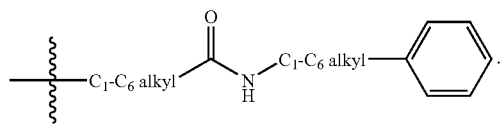

Abbreviations used in the specification, particularly the Schemes and Examples, are as follows:
CBz=Benzyloxycarbonyl
DAMGO=Tyr-D-Ala-Gly-N-methyl-Phe-Gly-ol
DIPEA=Diisopropylethylamine
DMF=N,N-Dimethylformamide
EDTA=Ethylenediaminetetraacetic acid
EtOH=Ethanol
Fmoc=9-Fluorenylmethoxycarbonyl
HEPES=4-(2-Hydroxyethyl)-1-piperizine ethane sulfonic acid
KO-t-Bu=Potassium t-butoxide
LiHMDS=Lithium bis(trimethylsilyl)amide
MeCN=Acetonitrile
MeOH=Methanol
NaHMDS=Sodium bis(trimethylsilyl)amide
NMP=N-methyl-2-pyrrolidinone
PEI=Polyethyleneimine
t-BOC or Boc=Tert-Butoxycarbonyl
Tf=Triflyl (—$SO_2$—$CF_3$)
Tea=Triethylamine
TFA=Trifluoroacetic Acid
THF=Tetrahydrofuran
TMS=Trimethylsilyl
Tris HCl=Tris[hydroxymethyl]aminomethyl hydrochloride The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

One skilled in the art will recognize that, where not otherwise specified, the reaction step(s) is performed under suitable conditions, according to known methods, to provide the desired product.

One skilled in the art will recognize that wherein a reaction step of the present invention may be carried out in a variety of solvents or solvent systems, said reaction step may also be carried out in a mixture of the suitable solvents or solvent systems.

One skilled in the art will recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2$=CH—$CH_2$—, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T. W. Greene & P. G. M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following:

acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Compounds of formula (II) wherein $R^0$ is selected from the group consisting of —CCH, halogen, hydroxy, —$N_3$, —OC(O)—$C_{1-4}$alkyl —$OSO_2$—$C_{1-4}$alkyl and —O-(2-tetrahydropyranyl) are intermediates in the synthesis of compounds of formula (I) wherein $R^3$ is selected from the group consisting of

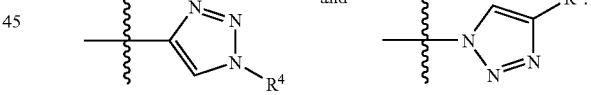

Compounds of formula (I) wherein $R^3$ is

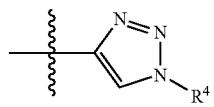

may be prepared according to the process as outlined in Scheme 1.

Scheme 1

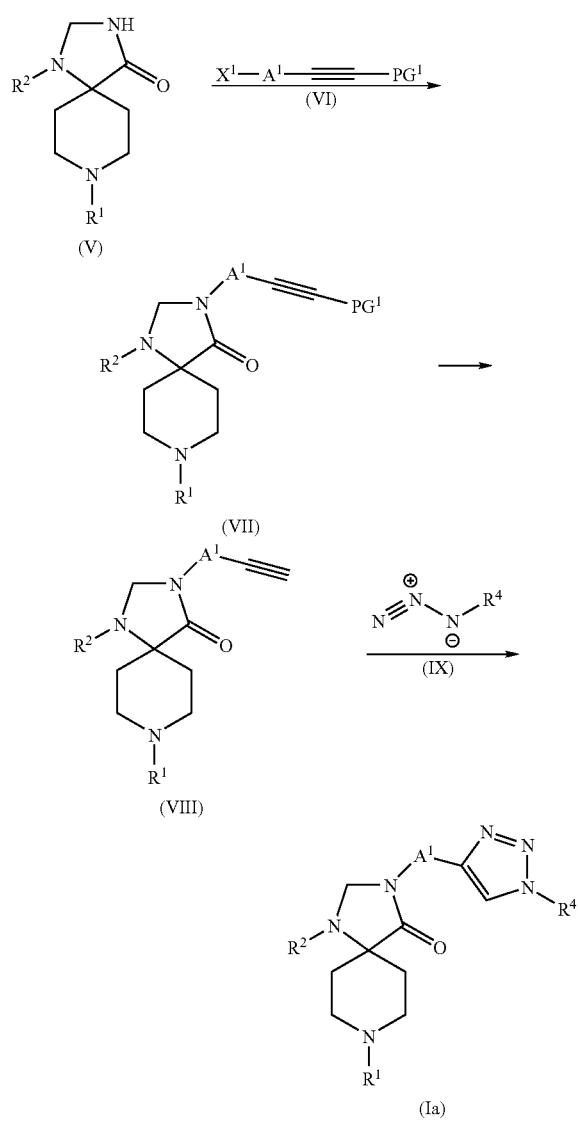

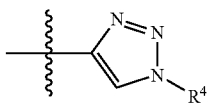

Accordingly, a suitably substituted compound of formula (V), a known compound or compound prepared according to known methods, is reacted with a suitably substituted compound of formula (VI), wherein $X^1$ is a suitably selected leaving group such as Cl, Br, I, tosylate, mesylate, and the like, preferably tosylate, and wherein $PG^1$ is a suitably selected protecting group such as trimethylsilyl, triethylsilyl, and the like, preferably trimethylsilyl, in the presence of a base such as NaH, KO-t-Bu, $K_2CO_3$, NaHMDS, LiHMDS, and the like, in an organic solvent such as NMP, DMF, THF, and the like, to yield the corresponding compound of formula (VII).

The compound of formula (VII) is de-protected according to known methods, to yield the corresponding compound of formula (VII). For example wherein $PG^1$ is trimethylsilyl or triethylsilyl, the compound of formula (VII) is de-protected by reacting with a base such as $K_2CO_3$, NaOH, LiOH, KF, and the like, in an organic solvent such as MeOH, THF, $H_2O$, and the like, to yield the corresponding compound of formula (VII).

One skilled in the art will recognize that the compound of formula (V) may alternatively be reacted with a compound of formula (VI) wherein $PG^1$ is hydrogen to yield the corresponding compound of formula (VII) without having to go through the de-protection step.

The compound of formula (VII) is reacted with a suitably substituted azide, a compound of formula (IX), a known compound or compound prepared by known methods, in the presence of a copper (I) source such as CuI, CuOTf, and the like, in the presence of a base, preferably an organic base, such as 2,6-lutidine, triethylamine, diisopropylethylamine, and the like, in an organic solvent such as water, MeOH, EtOH, MeCN, and the like, at a temperature in the range of from about 30° C. to about 120° C., preferably at a temperature in the range of from about room temperature to about 40° C., to yield the corresponding compound of formula (Ia).

Compounds of formula (I) wherein $R^3$ is

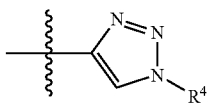

may alternatively be prepared according to the process as outlined in Scheme 2.

Scheme 2

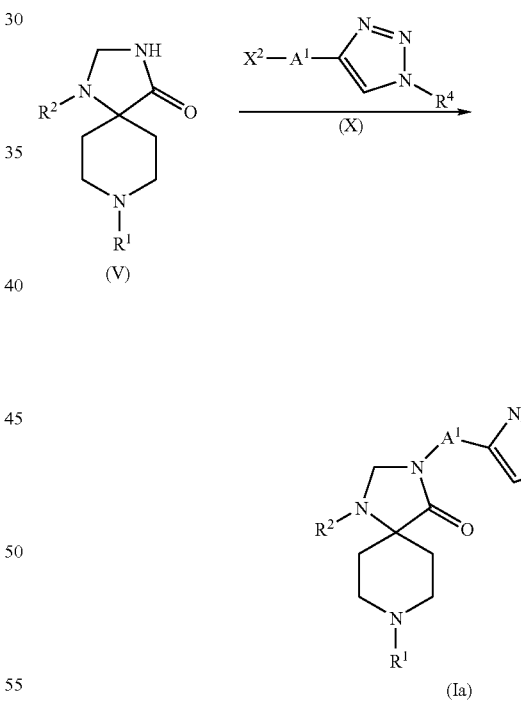

Accordingly, a suitably substituted compound of formula (V), a known compound or compound prepared by known methods, is reacted with a suitably substituted compound of formula (X), wherein $X^2$ is a suitably selected leaving group such as Cl, Br, I, tosylate, mesylate, and the like, a known compound or compound prepared by known methods, in the presence of a base such as NaH, KO-t-Bu, $K_2CO_3$, NaHMDS, LiHMDS, and the like, in an organic solvent such as NMP, DMF, THF, and the like, to yield the corresponding compound of formula (Ia).

Compounds of formula (I) wherein $R^3$ is

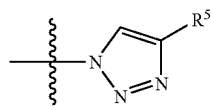

may be prepared according to the process outlined in Scheme 3.

Scheme 3

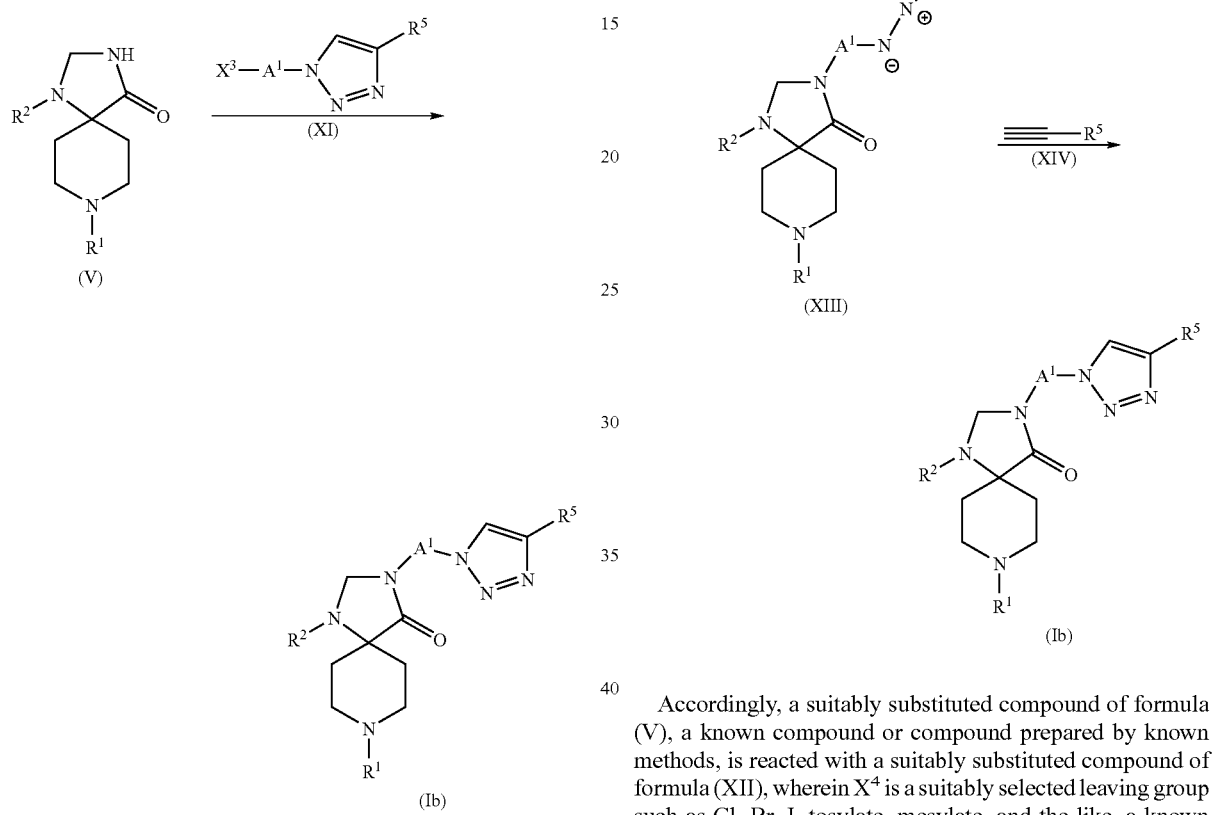

Accordingly, a suitably substituted compound of formula (V), a known compound or compound prepared by known methods, is reacted with a suitably substituted compound of formula (XI), wherein $X^3$ is a suitably selected leaving group such as Cl, Br, I, tosylate, mesylate, and the like, a known compound or compound prepared by known methods, in the presence of a base such as NaH, KO-t-Bu, $K_2CO_3$, NaHMDS, LiHMDS, and the like, in an organic solvent such as NMP, DMF, THF, and the like, to yield the corresponding compound of formula (Ib).

Compounds of formula (I) wherein $R^3$ is

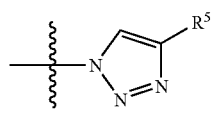

may alternatively be prepared according to the process outlined in Scheme 4.

Scheme 4

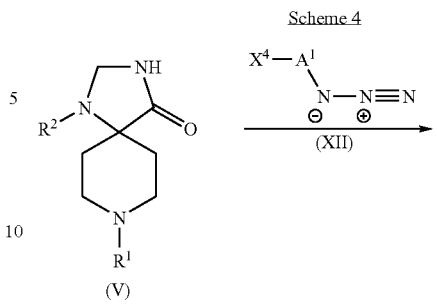

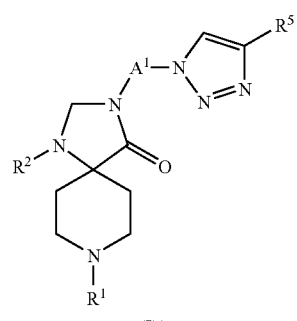

Accordingly, a suitably substituted compound of formula (V), a known compound or compound prepared by known methods, is reacted with a suitably substituted compound of formula (XII), wherein $X^4$ is a suitably selected leaving group such as Cl, Br, I, tosylate, mesylate, and the like, a known compound or compound prepared by known methods, in the presence of a base such as NaH, KO-t-Bu, $K_2CO_3$, NaHMDS, LiHMDS, and the like, in an organic solvent such as NMP, DMF, THF, and the like, to yield the corresponding compound of formula (XIII).

The compound of formula (XIII) is reacted with a suitably substituted acetylene, a compound of formula (XIV), in the presence of a copper (I) source such as CuI, CuOTf, and the like, in the presence of a base such as 2,6-lutidine, TEA, DIPEA, and the like, in an organic solvent such as water, MeOH, EtOH, MeCN, and the like, at a temperature in the range of from about 30° C. to about 120° C., to yield the corresponding compound of formula (Ib).

Compounds of formula (I) wherein $R^3$ is

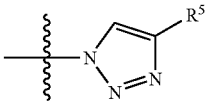

may alternatively be prepared according to the process outlined in Scheme 5.

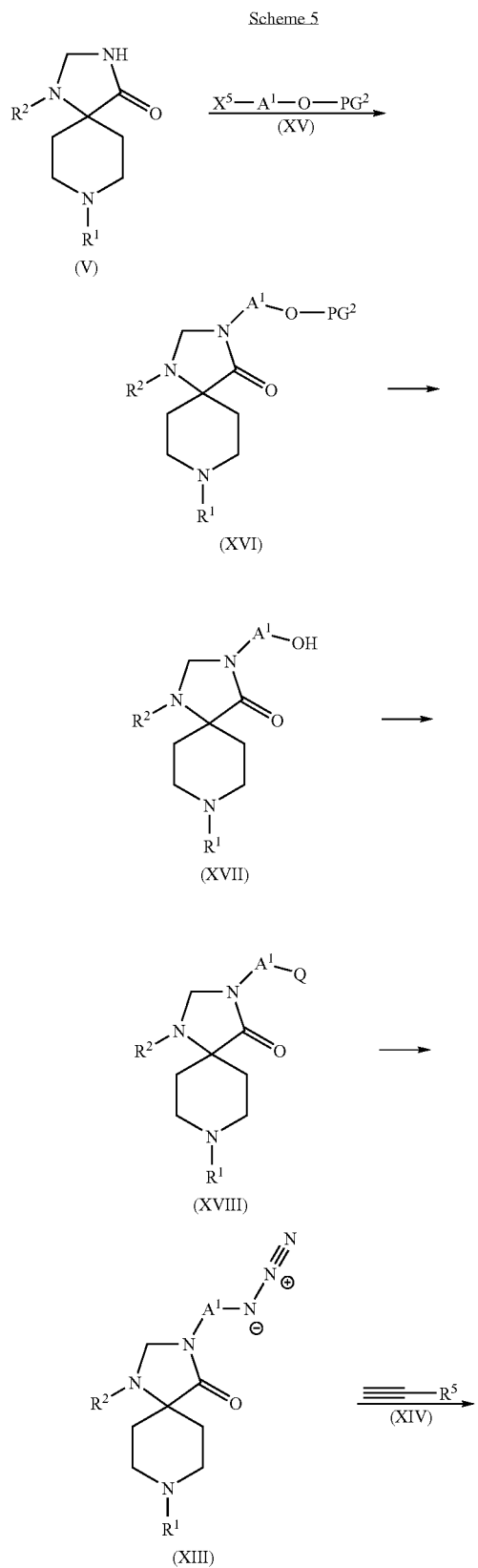
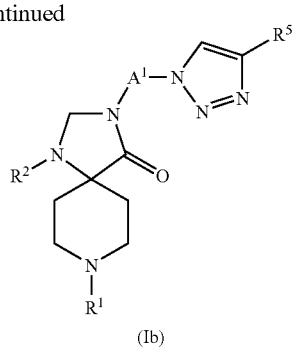

Accordingly, a suitably substituted compound of formula (IV), a known compound or compound prepared by known methods, is reacted with a suitably substituted compound of formula (XV), wherein $X^5$ is a suitable leaving group such as Cl, Br, I, tosylate, mesylate, and the like, and wherein $PG^2$ is a suitably selected protecting group such as methyl, acetyl, 2-tetrahydropyranyl, and the like, a known compound or compound prepared by known methods, in the presence of a base such as NaH, KO-t-Bu, $K_2CO_3$, NaHMDS, LiHMDS, and the like, in an organic solvent such as NMP, DMF, THF, and the like, to yield the corresponding compound of formula (XVI).

The compound of formula (XVI) is de-protected according to known methods to yield the corresponding compound of formula (XVII). For example, the compound of formula (XVI) may be de-protected by reacting with a base such as $K_2CO_3$, NaOH, LiOH, KF, and the like, or an acid such as HCl, TFA, and the like, in an organic solvent such as MeOH, THF, $H_2O$, and the like, to yield the corresponding compound of formula (XVII).

The compound of formula (XVII) is reacted with a suitably selected reagent which can introduce a nucleophilic leaving group such as methylsulfonyl chloride, para-toluenesulfonyl chloride, phosphorous tribromide, and the like, preferably, methylsulfonyl chloride, optionally in the presence of a base such as $K_2CO_3$, triethylamine, pyridine, and the like, in an organic solvent such as dichloromethane, THF, diethyl ether, and the like, to yield the corresponding compound of formula (XVIII), wherein Q is the corresponding nucleophilic leaving group. For example when the reagent, which can introduce a nucleophilic leaving group, is methylsulfonyl chloride, then Q in the compound of formula (XVIII) is —O—$SO_2$—$CH_3$. Similarly, when the reagent, which can introduce a nucleophilic leaving group, is para-toluenesulfonyl chloride, then Q in the compound of formula (XVIII) is —O—$SO_2$—(p-tolyl).

The compound of formula (XVIII) is reacted with a source of azide ($N_3$) such as sodium azide, triflyl azide, and the like, in an organic solvent such as dichloromethane, methanol, DMF, and the like, at a temperature in the range of from about 30° C. to about 120° C., to yield the corresponding compound of formula (XIII).

The compound of formula (XIII) is reacted with a suitably substituted acetylene, a compound of formula (XIV), in the presence of a copper (I) source such as CuI, CuOTf, and the like, in the presence of a base such as 2,6-lutidine, triethylamine, diisopropylethylamine, and the like, in an organic solvent such as water, MeOH, EtOH, MeCN, and the like, at a temperature in the range of from about 30° C. to about 120° C., to yield the corresponding compound of formula (Ib).

One skilled in the art will recognize that compounds of formula (II) wherein $R^0$ is selected from the group consisting of —CCH, —O—C(O)—C$_{1-4}$alkyl, —O—SO$_2$—C$_{1-4}$alkyl and —O-(2-tetrahydropyranyl) are intermediates in the preparation of compounds of formula (I) wherein R$^3$ is selected from the group consisting of

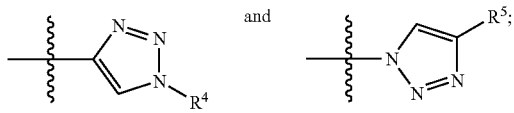

and may be prepared according to any of the processes described above, by selecting suitably substituted reagents and protecting groups PG$^1$ and/or PG$^2$.

One skilled in the art will recognize that in any of the processes outlined above, the N atom at the 8 position of the 1,3,8-triazaspiro[4.5]decan-4-one core may be optionally protected, according to known methods, with a suitably selected nitrogen protecting group as BOC, Fmoc, CBz, benzoyl, benzhydryl, and the like. One skilled in the art will further recognize that when such a protecting group is utilized, said protecting group is removed, according to known methods, at the appropriate point in the synthesis of the corresponding compound of formula (Ia) or compound of formula (Ib).

One skilled in the art will further recognize that the processes as described herein are regioselective (i.e. the processes as described herein yields the desired regioisomer of the 1,2,3-triazole in excess over the undesired regioisomer).

One skilled in the art will further recognize that wherein the processes as described in Schemes 1-5 above, compound of formula (V) is present in an enantiomeric excess (at the "*" position), then the product of formula (I) is therefore prepared as the correspond enantiomer.

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-1000 mg or any range therein, and may be given at a dosage of from about 0.01-300 mg/kg/day, or any range therein, preferably from about 0.5-50 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating disorders described in the present invention may also be carried out using a pharmaceutical composition comprising any of the compounds as defined herein and a pharmaceutically acceptable carrier. The pharmaceutical composition may contain between about 0.01 mg and 1000 mg of the compound, or any range therein; preferably about 10 to 500 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methylcellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations, which generally contain suitable preservatives, are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrol idone, pyran copolymer, polyhydroxypropylmethacrylam idephenol, polyhydroxy-ethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of disorders as described in the methods herein is required.

The daily dosage of the products may be varied over a wide range from 0.01 to 1,000 mg per adult human per day, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 300 mg/kg of body weight per day, or any range therein. Preferably, the range is from about 0.5 to about 50.0 mg/kg of body weight per day, or any range therein. More preferably, from about 1.0 to about 5.0 mg/kg of body weight per day, or any range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples, which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

8-(S)-Acenaphthen-1-yl-3-[2-(1-benzyl-1H-[1,2,3]triazol-4-yl)-ethyl]-1-(4-fluoro-phenyl)-1,3,8-triaza-spiro[4.5]decan-4-one (Compound #8)

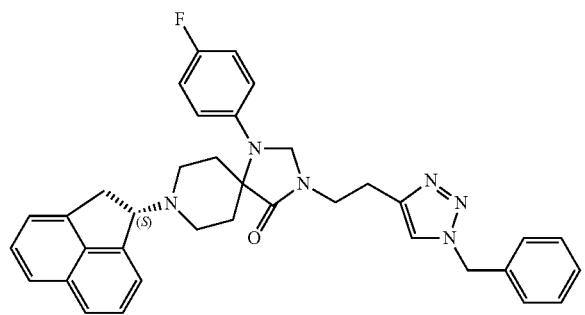

8-Acenaphthen-1-yl-1-(4-fluoro-phenyl)-1,3,8-triaza-spiro[4.5]decan-4-one (2.0 g, 4.98 mmol) was dissolved in THF (30 mL). To the reaction mixture was then added at 0° C. sodium hydride (60% in mineral oil, 219 mg, 5.47 mmol) under nitrogen atmosphere and the reaction mixture was stirred at 0° C. for one hour. To the reaction mixture was then added toluene-4-sulfonic acid but-3-ynyl ester (1.2 mL, 5.47 mmol). The reaction mixture was stirred at 0° C. and then warmed up to room temperature under nitrogen atmosphere for 10 hours, cooled down to at 0° C. and then partitioned with water and ethyl acetate. The organic layer was washed with brine, dried with $Na_2SO_4$, filtered and the solvent evaporated in vacuo to yield a crude oil. The crude oil was purified via flash chromatography (1.0% methanol/dichloromethane) to yield the 8-(S)-acenaphthen-1-yl-3-but-3-ynyl-1-(4-fluoro-phenyl)-1,3,8-triaza-spiro[4.5]decan-4-one as a foam.

$^1$H NMR (400 MHz, $CDCl_3$) δ7.68-7.66 (1H, m), 7.61-7.59 (1H, m), 7.54-7.50 (2H, m), 7.46-7.42 (1H, m), 7.27-7.25 (1H, m), 7.05-7.00 (2H, m), 6.98-6.94 (2H, m), 4.97-4.94 (1H, m), 4.75-4.73 (2H, m), 3.58-3.49 (3H, m), 3.39-3.32 (1H, m), 3.15-3.03 (2H, m), 2.82-2.79 (1H, m), 2.54-2.50 (2H, m), 2.44-2.36 (2H, m), 2.29-2.21 (1H. m), 1.99-1.97 (1H, m), 1.78-1.74 (1H, m), 1.68-1.63 (1H, m)

MS ($ES^+$) m/z 454.2 $(M+H)^+$.

8-(S)-Acenaphthen-1-yl-3-but-3-ynyl-1-(4-fluoro-phenyl)-1,3,8-triaza-spiro[4.5]decan-4-one (20 mg, 0.044 mmol) and benzyl azide (5.85 mg, 0.044 mmol) were suspended in a 1:1 mixture of ethanol and water (0.3 mL). Sodium ascorbate (0.0044 mmol, 5 μL of a freshly prepared 1.0M solution in water) was added, followed by copper (II) sulfate pentahydrate (0.1 mg, 0.4 μmol in 10 μL of water). The resulting heterogeneous mixture was stirred vigorously for 15 hours at room temperature and then partitioned with water and dichloromethane. The organic layer was washed with brine, dried with $Na_2SO_4$, filtered and the solvent evaporated in vacuo to yield a crude oil. The crude oil was purified via flash chromatography (60% ethyl acetate/hexanes) to yield the 8-(S)-acenaphthen-1-yl-3-but-3-ynyl-1-(4-fluoro-phenyl)-1,3,8-triaza-spiro[4.5]decan-4-one as a gum.

$^1$H NMR (400 MHz, $CDCl_3$) δ7.70-7.68 (1H, m), 7.62-7.60 (1H, m), 7.55-7.43 (3H, m), 7.31 (1H, s), 7.28-7.27 (1H, m), 7.13-7.12 (5H, m), 7.01-6.97 (2H, m), 6.87-6.84 (2H, m), 5.38-5.36 (m, 2H), 4.94-4.91 (1H, m), 4.52-4.51 (2H, m), 3.75-3.67 (2H, m), 3.52-3.47 (1H, m), 3.38-3.31 (1H, m), 3.43-3.02 (2H, t, J=Hz), 3.0-2.89 (2H, m), 2.73-2.70 (1H, m), 2.34-2.25 (2H, m), 2.16-2.09 (1H, m), 1.53-1.35 (2H, m)

MS ($ES^+$) m/z 587.1 $(M+H)^+$.

EXAMPLE 2

8-(S)-Acenaphthen-1-yl-3-(3-azido-propyl)-1-(4-fluoro-phenyl)-1,3,8-triaza-spiro[4.5]decan-4-one (Compound #14)

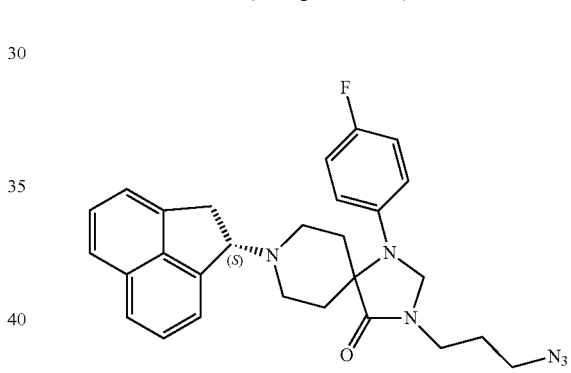

Toluene-4-sulfonic acid 3-azido-propyl ester was prepared as described in *Organic Letters* 2001, 3 (25), 4091-4094.

3-Bromo-propan-1-ol (5.56 g, 40 mmol) and triethylamine (5.56 g, 55 mmol) were dissolved in dichloromethane. To the reaction mixture was then added, at 0° C., acetyl chloride (3.6 g, 44 mmol) under nitrogen atmosphere and the reaction mixture was then stirred for one hour at 0° C. and for 3 hours at room temperature. The reaction mixture was then washed with aqueous 1N HCl, aqueous 1N NaOH, dried with $Na_2SO_4$, filtered and the solvent evaporated in vacuo to yield acetic acid 3-bromo-propyl ester (7.2 g) which was used in the next step without further purification.

Acetic acid 3-bromo-propyl ester (6.7 g, 37 mmol) was suspended in water (50 mL) and tert-butanol (20 mL). To the resulting mixture was then added sodium azide (2.76 g, 42.6 mmol) and the reaction mixture was heated to reflux for 18 hours, then concentrated to half of its volume. The reaction mixture was partitioned with water and ethyl acetate. The organic layer was washed with water, dried with $Na_2SO_4$, filtered and the solvent evaporated in vacuo to yield the acetic acid 3-azido-propyl ester (3.16 g) as an oil which used in the next step without further purification.

Acetic acid 3-azido-propyl ester (3.16 g, 22.1 mmol) was dissolved in water (25 mL) and methanol (25 mL). To the resulting mixture was then added potassium carbonate (3.81 g, 27.6 mmol) and the resulting solution was stirred for 2 hours at room temperature, reduced to a third of its volume, saturated with MgSO$_4$, filtered and partitioned with water and dichloromethane. The organic layer was dried with magnesium sulfate, filtered and transferred into to dry round bottom flask. To the filtrate was then added (3.35 g, 33.1 mmol) and tosyl chloride (4.6 g, 24.3 mmol) and the reaction mixture was stirred at room temperature for 24 hours. The reaction mixture was partitioned with aqueous 1N HCl and dichloromethane. The organic layer was dried with Na$_2$SO$_4$, filtered and the solvent evaporated in vacuo to yield a crude oil. The crude oil was purified via flash chromatography (10% ethyl acetate/hexanes) to yield the toluene-4-sulfonic acid 3-azido-propyl ester (2.03 g) as an oil.

8-(S)-Acenaphthen-1-yl-1-(4-fluoro-phenyl)-1,3,8-triaza-spiro[4.5]decan-4-one (1.0 g, 2.5 mmol) was dissolved in THF (12 mL). To the reaction mixture was then added at 0° C. sodium hydride (60% in mineral oil, 110 mg, 2.74 mmol) under nitrogen atmosphere and the reaction mixture was stirred at room temperature for 0.5 hour. To the reaction mixture was then added toluene-4-sulfonic acid 3-azido-propyl ester (0.66 g, 2.61 mmol) in THF (2 mL) followed by tetrabutylammonium iodide (0.18 g, 0.5 mmol) and DMF (2 mL). The reaction mixture was then heated at 60° C. for 4 hours, for 15 hours at 40° C. and then partitioned with water and dichloromethane. The organic layer was washed with brine, dried with Na$_2$SO$_4$, filtered and the solvent evaporated in vacuo to yield a crude oil. The crude oil was purified via flash chromatography (1% methanol/dichloromethane) to yield the 8-(S)-acenaphthen-1-yl-3-(3-azido-propyl)-1-(4-fluoro-phenyl)-1,3,8-triaza-spiro[4.5]decan-4-one (0.94 g) as a foam.

$^1$H NMR (400 MHz, CDCl$_3$) δ7.69-7.67 (1H, m), 7.61-7.59 (1H, m), 7.53-7.50 (2H, m), 7.46-7.42 (1H, m), 7.28-7.27 (1H, m), 7.06-7.01 (2H, m), 6.97-6.94 (2H, m), 4.97-4.95 (1H, m), 4.62 (2H, s), 3.57-3.50 (2H, m), 3.47 (2H, t, J=8.0 Hz), 3.37 (2H, t, J=6.3 Hz), 3.17-3.05 (2H, m), 2.86-2.82 (1H, m), 2.46-2.39 (2H, m), 2.29-2.26 (1H, m), 1.91-1.84 (2H, m), 1.75-1.62 (2H, m)

MS (ES$^+$) m/z 485.1 (M+H)$^+$.

EXAMPLE 3

8-(R)-Acenaphthen-1-yl-3-(3-azido-propyl)-1-(4-fluoro-phenyl)-1,3,8-triaza-spiro[4.5]decan-4-one (Compound #16)

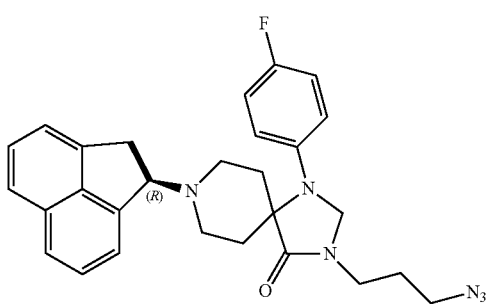

8-(R)-Acenaphthen-1-yl-3-(3-azido-propyl)-1-(4-fluoro-phenyl)-1,3,8-triaza-spiro[4.5]decan-4-one was prepared according to the procedure as described in Example 2 above.
MS (ES$^+$) m/z 485.1 (M+H)$^+$.

NMR and Mass was the same for the compounds prepared in Example 2 and 3, as they are enantiomer of each other.

EXAMPLE 4

8-(R)-Acenaphthen-1-yl-3-(2-azido-ethyl)-1-(4-fluoro-phenyl)-1,3,8-triaza-spiro[4.5]decan-4-one (Compound #19)

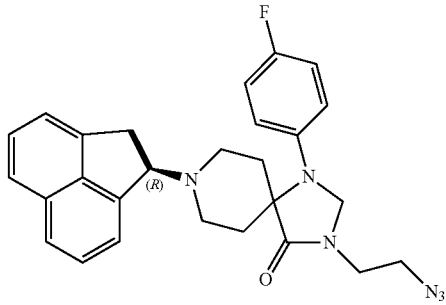

8-(S)-Acenaphthen-1-yl-1-(4-fluoro-phenyl)-1,3,8-triaza-spiro[4.5]decan-4-one (1.0 g, 2.5 mmol) was dissolved in DMF (10 mL). To the reaction mixture was then added at 0° C. sodium hydride (60% in mineral oil, 110 mg, 2.74 mmol) under nitrogen atmosphere and the reaction mixture was stirred at 0° C. for 0.5 hour. To the reaction mixture was then added 2-(2-bromo-ethoxy)-tetrahydro-pyran (0.54 g, 2.61 mmol) at 0° C. The reaction mixture was stirred at 0° C. for 1 hour, at room temperature for 16 hours and then partitioned with water and dichloromethane. The organic layer was washed with brine, dried with Na$_2$SO$_4$, filtered and the solvent evaporated in vacuo to yield a crude oil. The crude oil was purified via flash chromatography (1% methanol/dichloromethane) to yield the 8-(R)-Acenaphthen-1-yl-1-(4-fluoro-phenyl)-3-[2-(tetrahydro-pyran-2-yloxy)-ethyl]-1,3,8-triaza-spiro[4.5]decan-4-one (0.735 g) as a foam.

$^1$H NMR (400 MHz, CDCl$_3$) δ7.68-7.66 (1H, m), 7.61-7.59 (1H, m), 7.52-7.50 (2H, m), 7.46-7.42 (1H, m), 7.27-7.25 (1H, m), 7.04-6.99 (2H, m), 6.97-6.92 (2H, m), 4.97-4.94 (1H, m), 4.73 (2H, s), 4.58 (1H, br s), 3.94-3.90 (1H, m), 3.81-3.76 (1H, m), 3.67-3.47 (5H, m), 3.39-3.29 (1H, m), 3.15-3.04 (2H, m), 2.82-2.79 (1H, m), 2.43-2.36 (2H, m), 2.28-2.21 (1H, m), 1.75-1.71 (2H, m), 1.70-1.62 (2H, m), 1.56-1.46 (4H, m)

MS (ES$^+$) m/z 530.1 (M+H)$^+$.

8-(R)-Acenaphthen-1-yl-1-(4-fluoro-phenyl)-3-[2-(tetrahydro-pyran-2-yloxy)-ethyl]-1,3,8-triaza-spiro[4.5]decan-4-one (0.735 g, 1.37 mmol) was dissolved in methanol (35 mL). To the reaction mixture was then added aqueous 1N HCl (14 mL) and the reaction mixture was stirred at room temperature for 2 hours. The reaction mixture was then concentrated in vacuo and the aqueous layer neutralized with an aqueous saturated solution of sodium carbonate. The resulting solution was partitioned with water and dichloromethane. The organic layer was washed with brine, dried with Na$_2$SO$_4$, filtered and the solvent evaporated in vacuo to yield the 8-(R)-acenaphthen-1-yl-1-(4-fluoro-phenyl)-3-(2-hydroxy-ethyl)-1,3,8-triaza-spiro[4.5]decan-4-one (0.636 g) as a foam.

$^1$H NMR (400 MHz, CDCl$_3$) δ7.68-7.66 (1H, m), 7.61-7.59 (1H, m), 7.54-7.50 (2H, m), 7.46-7.42 (1H, m), 7.26-7.25 (1H, m), 7.04-6.99 (2H, m), 6.97-6.95 (2H, m), 4.96-4.93 (1H, m), 4.72-4.70 (2H, m), 3.86-3.83 (2H, m), 3.56-3.49 (3H, m), 3.39-3.33 (1H, m), 3.14-3.02 (2H, m), 2.82-

2.79 (1H, m), 2.51 (1H, br s), 2.44-2.35 (2H, m), 2.27-2.20 (1H, m), 1.78-1.75 (1H, m), 1.68-1.65 (1H, m)

MS (ES$^+$) m/z 446.1 (M+H)$^+$.

8-(R)-acenaphthen-1-yl-1-(4-fluoro-phenyl)-3-(2-hydroxy-ethyl)-1,3,8-triaza-spiro[4.5]decan-4-one (0.7 g, 1.57 mmol) and triethylamine (0.25 g, 2.51 mmol) were dissolved in dichloromethane (15 mL). To the reaction mixture was then added, at 0° C., methanesulfonyl chloride (0.225 g, 1.96 mmol) under nitrogen atmosphere and the reaction mixture was stirred 0.5 hour at 0° C. then for 1 hour at room temperature. The resulting solution was partitioned with aqueous saturated NaHCO$_3$ and dichloromethane. The organic layer was washed with brine, dried with Na$_2$SO$_4$, filtered and the solvent evaporated in vacuo to yield a crude oil. The crude oil was purified via flash chromatography (3% methanol/dichloromethane) to yield methanesulfonic acid 2-[8-acenaphthen-1-yl-1-(4-fluoro-phenyl)-4-oxo-1,3,8-triaza-spiro[4.5]dec-3-yl]-ethyl ester (0.75 g) as a foam.

$^1$H NMR (400 MHz, CDCl$_3$) δ7.68-7.66 (1H, m), 7.61-7.59 (1H, m), 7.53-7.50 (2H, m), 7.46-7.42 (1H, m), 7.27-7.25 (1H, m), 7.05-6.96 (4H, m), 4.95-4.94 (1H, m), 4.72 (2H, s), 4.42-4.40 (2H, m), 3.74-3.71 (2H, m), 3.53-3.47 (1H, m), 3.39-3.33 (1H, m), 3.10-3.02 (2H, m), 3.01 (3H, s), 2.85-2.79 (1H, m), 2.45-2.42 (1H, m), 2.35-2.30 (1H, m), 2.21-2.16 (1H, m), 1.78-1.75 (1H, m), 1.69-1.66 (1H, m)

MS (ES$^+$) m/z 524.1 (M+H)$^+$.

Methanesulfonic acid 2-[8-acenaphthen-1-yl-1-(4-fluoro-phenyl)-4-oxo-1,3,8-triaza-spiro[4.5]dec-3-yl]-ethyl ester (0.75 g, 1.43 mmol) was dissolved in DMF (16 mL). The reaction mixture was then added to a solution sodium azide (0.28 g, 4.29 mmol) and the resulting mixture was heated in a pressure vessel at 100° C. for 2 hours, cooled down to room temperature and then partitioned with icy water/brine and dichloromethane. The organic layer was washed with brine, dried with Na$_2$SO$_4$, filtered and the solvent evaporated in vacuo to yield a crude oil. The crude oil was purified via flash chromatography (2% methanol/dichloromethane) to yield the 8-(R)-acenaphthen-1-yl-3-(2-azido-ethyl)-1-(4-fluoro-phenyl)-1,3,8-triaza-spiro[4.5]decan-4-one (0.65 g) as a foam.

$^1$H NMR (400 MHz, CDCl$_3$) δ7.68-7.66 (1H, m), 7.61-7.59 (1H, m), 7.54-7.50 (2H, m), 7.46-7.42 (1H, m), 7.27-7.26 (1H, m), 7.05-6.95 (4H, m), 4.96-4.94 (1H, m), 4.71-4.69 (2H, m), 3.57-3.50 (5H, m), 3.39-3.33 (1H, m), 3.14-3.03 (2H, m), 2.83-2.80 (1H, m), 2.45-2.34 (2H, m), 2.26-2.20 (1H, m), 1.79-1.64 (2H, m)

MS (ES$^+$) m/z 471.1 (M+H)$^+$.

EXAMPLE 5

8-(S)-Acenaphthen-1-yl-3-(2-azido-ethyl)-1-(4-fluoro-phenyl)-1,3,8-triaza-spiro[4.5]decan-4-one (Compound #18)

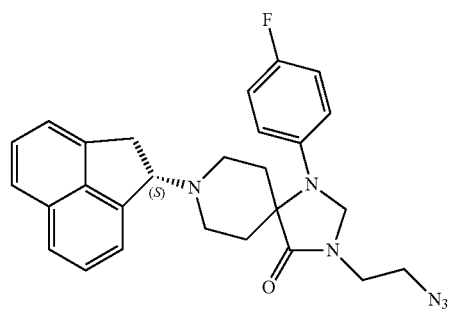

8-(S)-Acenaphthen-1-yl-3-(2-azido-ethyl)-1-(4-fluoro-phenyl)-1,3,8-triaza-spiro[4.5]decan-4-one was prepared according to the procedure as described in Example 4 above.

MS (ES$^+$) m/z 471.1 (M+H)$^+$.

NMR and Mass was the same for the compounds prepared in Example 4 and 5, as they are enantiomer of each other.

EXAMPLE 6

8-(S)-Acenaphthen-1-yl-1-(4-fluoro-phenyl)-3-{3-[4-(3-fluoro-phenyl)[1,2,3]triazol-1-yl]-propyl}-1,3,8-triaza-spiro[4.5]decan-4-one (Compound #30)

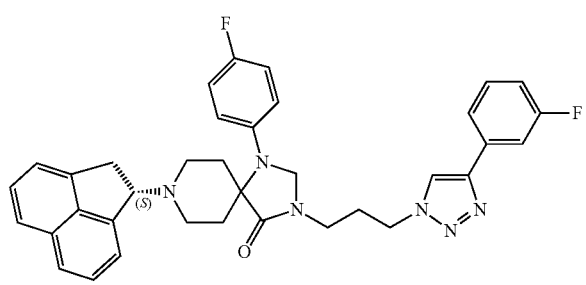

8-(S)-acenaphthen-1-yl-3-(3-azido-propyl)-1-(4-fluoro-phenyl)-1,3,8-triaza-spiro[4.5]decan-4-one (25 mg, 0.051 mmol) and 1-ethynyl-3-fluoro-benzene (6.18 mg, 0.051 mmol) were suspended in a mixture of ethanol (0.3 mL) and an aqueous solution of copper (II) sulfate pentahydrate (0.1 mg, 0.5 μmol in 150 μL of water). The resulting mixture was then was added to sodium ascorbate (0.005 mmol, 5 μL of a freshly prepared 1.0M solution in water). The resulting heterogeneous mixture was stirred vigorously for 15 hours at about 25-30° C. and then partitioned with water and dichloromethane. The organic layer was washed with brine, dried with Na$_2$SO$_4$, filtered and the solvent evaporated in vacuo to yield a crude oil. The crude oil was purified via flash chromatography (70% ethyl acetate/hexanes) to yield the 8-(S)-acenaphthen-1-yl-1-(4-fluoro-phenyl)-3-{3-[4-(3-fluoro-phenyl)[1,2,3]triazol-1-yl]-propyl}-1,3,8-triaza-spiro[4.5]decan-4-one (0.019 g) as a gum.

$^1$H NMR (400 MHz, CDCl$_3$) δ 7.97 (1H, s), 7.69-7.67 (1H, m), 7.62-7.56 (3H, m), 7.55-7.50 (2H, m), 7.46-7.43 (1H, m), 7.37-7.32 (1H, m), 7.28-7.26 (1H, m), 7.05-7.00 (3H, m), 6.97-6.93 (2H, m), 4.97-4.94 (1H, m), 4.64-4.62 (2H, m), 4.44 (2H, t, J=6.6 Hz), 3.54-3.46 (3H, m), 3.41-3.35 (1H, m), 3.11-3.06 (2H, m), 2.80-2.77 (1H, m), 2.44-2.22 (5H, m), 1.74-1.60 (2H, m)

MS (ES$^+$) m/z 605.2 (M+H)$^+$.

EXAMPLE 7

8-(R)-Acenaphthen-1-yl-1-(4-fluoro-phenyl)-3-{3-[4-(3-fluoro-phenyl)[1,2,3]triazol-1-yl]-propyl}-1,3,8-triaza-spiro[4.5]decan-4-one (Compound #31)

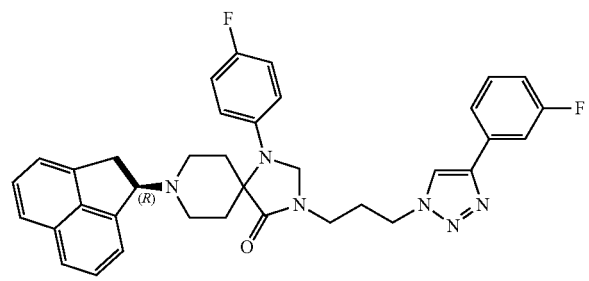

8-(R)-Acenaphthen-1-yl-1-(4-fluoro-phenyl)-3-{3-[4-(3-fluoro-phenyl)[1,2,3]triazol-1-yl]-propyl}-1,3,8-triaza-spiro[4.5]decan-4-one was prepared according to the procedure as described in Example 6 above.

MS (ES$^+$) m/z 471.1 (M+H)$^+$.

EXAMPLE 8

8-(R)-Acenaphthen-1-yl-1-(4-fluoro-phenyl)-3-[3-(4-hydroxymethyl-[1,2,3]triazol-1-yl)-propyl]-1,3,8-triaza-spiro[4.5]decan-4-one (Compound #33)

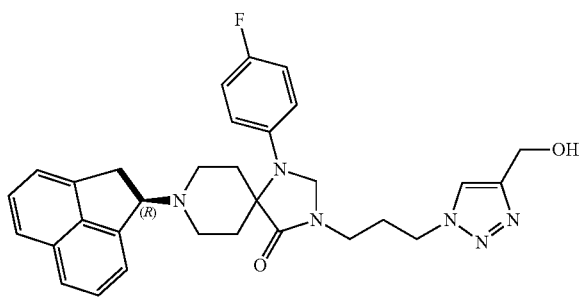

8-(R)-Acenaphthen-1-yl-1-(4-fluoro-phenyl)-3-[3-(4-hydroxymethyl-[1,2,3]triazol-1-yl)-propyl]-1,3,8-triaza-spiro[4.5]decan-4-one was prepared according to the procedure as described in Example 6 above.

$^1$H NMR (400 MHz, CDCl$_3$) δ 7.70 (1H, s), 7.69-7.67 (1H, m), 7.62-7.60 (1H, m), 7.54-7.51 (2H, m), 7.46-7.42 (1H, m), 7.28-7.26 (1H, m), 7.05-7.01 (2H, m), 6.97-6.94 (2H, m), 4.96-4.94 (1H, m), 4.79 (2H, s), 4.63-4.61 (2H, m), 4.40-4.37 (2H, m), 3.55-3.49 (1H, m), 3.42-3.33 (3H, m), 3.12-3.02 (2H, m), 2.83-2.780 (1H, m), 2.45-2.35 (2H, m), 2.27-2.20 (3H, m), 1.73-1.61 (2H, m)

MS (ES$^+$) m/z 541.2 (M+H)$^+$.

EXAMPLE 9

8-(S)-Acenaphthen-1-yl-1-(4-fluoro-phenyl)-3-[3-(4-hydroxymethyl-[1,2,3]triazol-1-yl)-propyl]-1,3,8-triaza-spiro[4.5]decan-4-one (Compound #32)

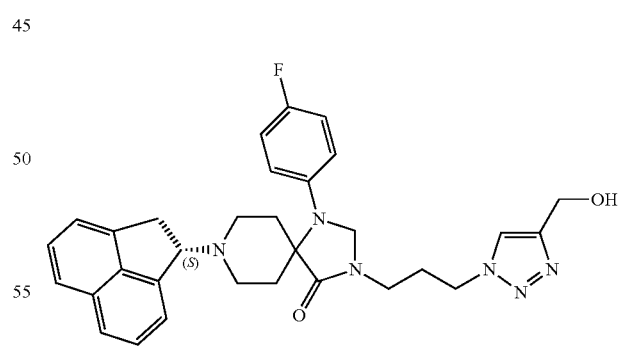

8-(S)-Acenaphthen-1-yl-1-(4-fluoro-phenyl)-3-[3-(4-hydroxymethyl-[1,2,3]triazol-1-yl)-propyl]-1,3,8-triaza-spiro[4.5]decan-4-one was prepared according to the procedure as described in Example 6 above.

MS (ES$^+$) m/z 541.2 (M+H)$^+$.

EXAMPLE 10

8-(S)-Acenaphthen-1-yl-1-(4-fluoro-phenyl)-3-[3-(4-methylaminomethyl-[1,2,3]triazol-1-yl)-propyl]-1,3,8-triaza-spiro[4.5]decan-4-one (Compound #34)

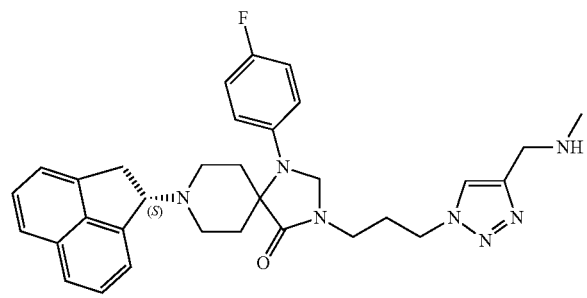

8-(S)-Acenaphthen-1-yl-1-(4-fluoro-phenyl)-3-[3-(4-methylaminomethyl-[1,2,3]triazol-1-yl)-propyl]-1,3,8-triaza-spiro[4.5]decan-4-one was prepared according to the procedure as described in Example 6 above.

$^1$H NMR (400 MHz, CDCl$_3$) δ 7.69-7.67 (1H, m), 7.61-7.59 (2H, m), 7.52-7.51 (2H, m), 7.46-7.42 (1H, m), 7.28-7.26 (1H, m), 7.05-7.01 (2H, m), 6.97-6.94 (2H, m), 4.97-4.94 (1H, m), 4.63-4.61 (2H, m), 4.40-4.37 (2H, m), 3.86 (2H, br s), 3.55-3.50 (1H, m), 3.48-3.34 (3H, m), 3.11-3.03 (2H, m), 2.83-2.81 (1H, m), 2.47-2.37 (5H, m), 2.29-2.22 (2H, m), 1.74-1.61 (2H, m)

MS (ES$^+$) m/z 554.2 (M+H)$^+$.

EXAMPLE 11

8-(R)-Acenaphthen-1-yl-1-(4-fluoro-phenyl)-3-[3-(4-methylaminomethyl-[1,2,3]triazol-1-yl)-propyl]-1,3,8-triaza-spiro[4.5]decan-4-one (Compound #35)

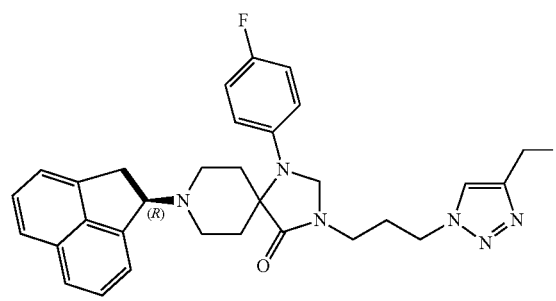

8-(R)-Acenaphthen-1-yl-1-(4-fluoro-phenyl)-3-[3-(4-methylaminomethyl-[1,2,3]triazol-1-yl)-propyl]-1,3,8-triaza-spiro[4.5]decan-4-one was prepared according to the procedure as described in Example 6 above.

MS (ES$^+$) m/z 554.2 (M+H)$^+$.

EXAMPLE 12

1-{3-[8-(S)-Acenaphthen-1-yl-1-(4-fluoro-phenyl)-4-oxo-1,3,8-triaza-spiro[4.5]dec-3-yl]-propyl}-1H-[1,2,3]triazole-4-carboxylic acid ethyl ester (Compound #36)

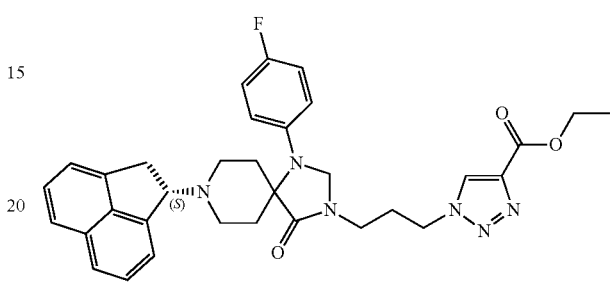

1-{3-[8-(S)-Acenaphthen-1-yl-1-(4-fluoro-phenyl)-4-oxo-1,3,8-triaza-spiro[4.5]dec-3-yl]-propyl}-1H-[1,2,3]triazole-4-carboxylic acid ethyl ester was according to the procedure as described in Example 6 above.

MS (ES$^+$) m/z 583.2 (M+H)$^+$.

EXAMPLE 13

1-{3-[8-(R)-Acenaphthen-1-yl-1-(4-fluoro-phenyl)-4-oxo-1,3,8-triaza-spiro[4.5]dec-3-yl]-propyl}-1H-[1,2,3]triazole-4-carboxylic acid ethyl ester (Compound #37)

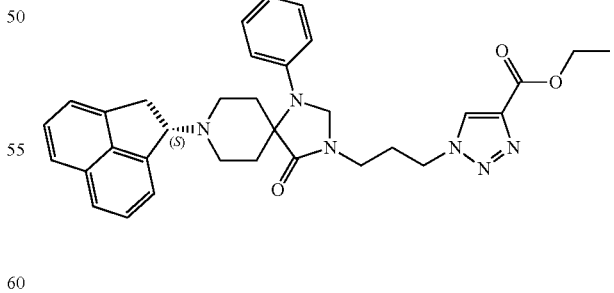

1-{3-[8-(R)-Acenaphthen-1-yl-1-(4-fluoro-phenyl)-4-oxo-1,3,8-triaza-spiro[4.5]dec-3-yl]-propyl}-1H-[1,2,3]triazole-4-carboxylic acid ethyl ester was prepared according to the procedure as described in Example 6 above.

MS (ES$^+$) m/z 583.2 (M+H)$^+$.

EXAMPLE 14

8-(R)-Acenaphthen-1-yl-1-(4-fluoro-phenyl)-3-{2-[4-(3-methyl-3H-imidazol-4-yl)-[1,2,3]triazol-1-yl]-ethyl}-1,3,8-triaza-spiro[4.5]decan-4-one (Compound #38)

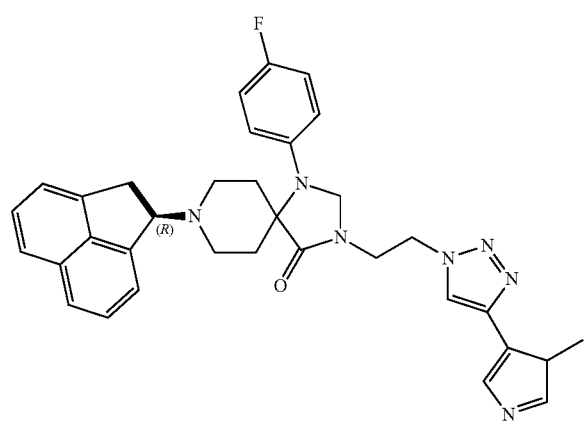

8-(R)-acenaphthen-1-yl-3-(2-azido-ethyl)-1-(4-fluoro-phenyl)-1,3,8-triaza-spiro[4.5]decan-4-one (40 mg, 0.085 mmol) and 5-ethynyl-1-methyl-1H-imidazole (9 mg, 0.085 mmol) were suspended in a mixture of ethanol (0.6 mL) and an aqueous solution of copper (II) sulfate pentahydrate (0.5 mg, 2 μmol in 0.4 mL of water). The resulting mixture was then added to sodium ascorbate (1.7 mg, 10 μmol, 10 μL of a freshly prepared 1.0M solution in water). The resulting heterogeneous mixture was stirred vigorously for 15 hours at about 25-30° C. and then partitioned with water and dichloromethane. The organic layer was washed with brine, dried with $Na_2SO_4$, filtered and the solvent evaporated in vacuo to yield a crude oil. The crude oil was purified via flash chromatography (2.5% MeOH in ammonia 2.0M/$CH_2Cl_2$) to yield the 8-(R)-Acenaphthen-1-yl-1-(4-fluoro-phenyl)-3-{2-[4-(3-methyl-3H-imidazol-4-yl)-[1,2,3]triazol-1-yl]-ethyl}-1,3,8-triaza-spiro[4.5]decan-4-one (0.026 g) as a gum.

$^1$H NMR (400 MHz, $CDCl_3$) δ 7.73 (1H, s), 7.68-7.66 (1H, m), 7.62-7.60 (1H, m), 7.52-7.48 (1H, m), 7.47-7.42 (3H, m), 7.27-7.25 (1H, m), 7.19 (1H, br s), 7.02-6.97 (2H, m), 6.91-6.88 (2H, m), 4.92-4.89 (1H, m), 4.70-4.66 (2H, m), 4.46 (2H, s), 3.95-3.91 (2H, m), 3.70 (3H, s), 3.49-3.30 (2H, m), 2.99-2.90 (2H, m), 2.74-2.71 (1H, m), 2.39-2.36 (1H, m), 2.26-2.19 (1H, m), 2.12-2.05 (1H, m), 1.64-1.54 (1H, m)

MS ($ES^+$) m/z 577.2 $(M+H)^+$.

EXAMPLE 15

8-(S)-Acenaphthen-1-yl-1-(4-fluoro-phenyl)-3-{2-[4-(3-methyl-3H-imidazol-4-yl)-[1,2,3]triazol-1-yl]-ethyl}-1,3,8-triaza-spiro[4.5]decan-4-one (Compound #39)

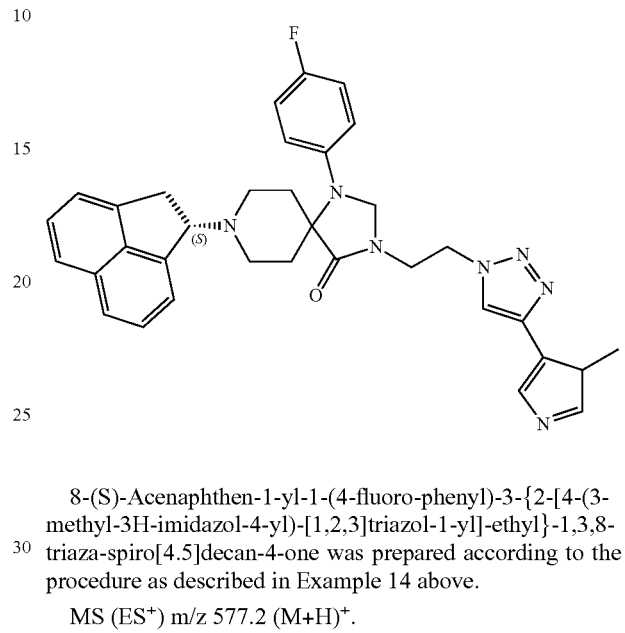

8-(S)-Acenaphthen-1-yl-1-(4-fluoro-phenyl)-3-{2-[4-(3-methyl-3H-imidazol-4-yl)-[1,2,3]triazol-1-yl]-ethyl}-1,3,8-triaza-spiro[4.5]decan-4-one was prepared according to the procedure as described in Example 14 above.

MS ($ES^+$) m/z 577.2 $(M+H)^+$.

EXAMPLE 16

8-(R)-Acenaphthen-1-yl-1-(4-fluoro-phenyl)-3-[2-(4-pyridin-3-yl-[1,2,3]triazol-1-yl)-ethyl]-1,3,8-triaza-spiro[4.5]decan-4-one (Compound #40)

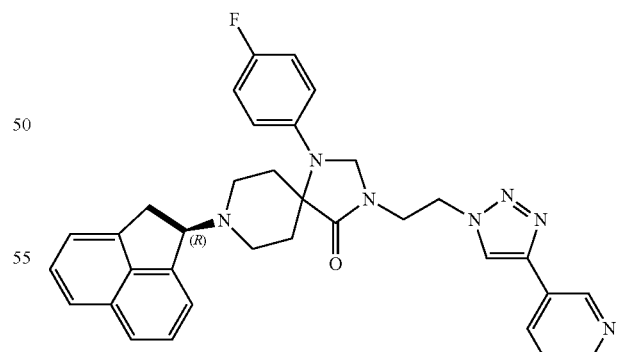

8-(R)-Acenaphthen-1-yl-1-(4-fluoro-phenyl)-3-[2-(4-pyridin-3-yl-[1,2,3]triazol-1-yl)-ethyl]-1,3,8-triaza-spiro[4.5]decan-4-one was prepared according to the procedure as described in Example 14 above.

MS ($ES^+$) m/z 574.2 $(M+H)^+$.

EXAMPLE 17

8-(S)-Acenaphthen-1-yl-1-(4-fluoro-phenyl)-3-[2-(4-pyridin-3-yl-[1,2,3]triazol-1-yl)-ethyl]-1,3,8-triaza-spiro[4.5]decan-4-one (Compound #41)

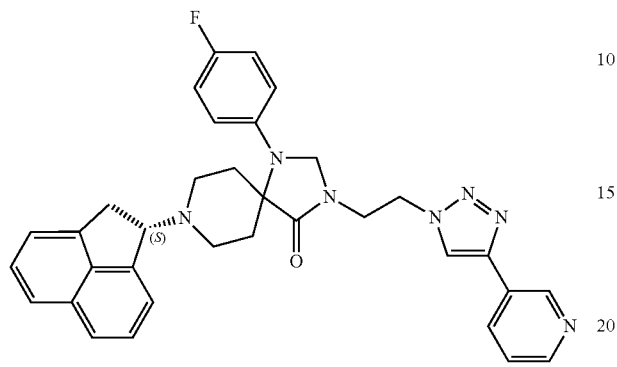

8-(S)-Acenaphthen-1-yl-1-(4-fluoro-phenyl)-3-[2-(4-pyridin-3-yl-[1,2,3]triazol-1-yl)-ethyl]-1,3,8-triaza-spiro[4.5]decan-4-one prepared according to the procedure as described in Example 14 above.
MS (ES$^+$) m/z 574.2 (M+H)$^+$.

EXAMPLE 18

8-(S)-Acenaphthen-1-yl-1-(4-fluoro-phenyl)-3-[2-(4-methylaminomethyl-[1,2,3]triazol-1-yl)-ethyl]-1,3,8-triaza-spiro[4.5]decan-4-one (Compound #21)

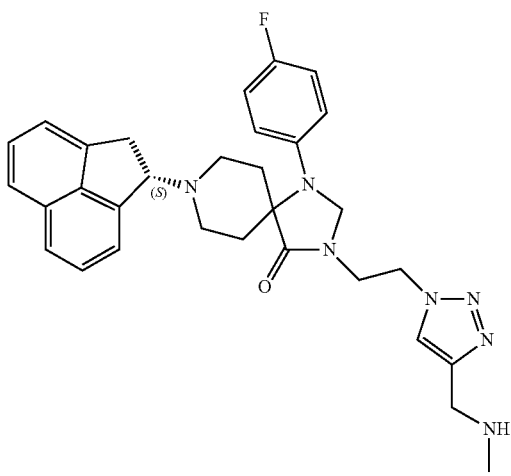

8-(S)-Acenaphthen-1-yl-1-(4-fluoro-phenyl)-3-[2-(4-methylaminomethyl-[1,2,3]triazol-1-yl)-ethyl]-1,3,8-triaza-spiro[4.5]decan-4-one was prepared according to the procedure as described in Example 14 above.
$^1$H NMR (400 MHz, CDCl$_3$) δ7.68-7.66 (1H, m), 7.61-7.59 (1H, m), 7.53-7.47 (3H, m), 7.46-7.42 (1H, m), 7.27-7.25 (1H, m), 7.01-6.97 (2H, m), 6.90-6.86 (2H, m), 4.93-4.91 (1H, m), 4.61-4.58 (2H, m), 4.38-4.35 (2H, m), 3.89-3.86 (2H, m), 3.76 (3H, s), 3.46 (2H, s), 3.38-3.32 (1H, m), 3.02-2.94 (2H, m), 2.78-2.75 (1H, m), 2.41-2.35 (3H, m), 2.28-2.21 (1H, m), 2.15-2.07 (1H, m), 1.66-1.62 (1H, m), 1.56-1.53 (1H, m)
MS (ES$^+$) m/z 540.4 (M+H)$^+$.

EXAMPLE 19

8-(R)-Acenaphthen-1-yl-1-(4-fluoro-phenyl)-3-[2-(4-methylaminomethyl-[1,2,3]triazol-1-yl)-ethyl]-1,3,8-triaza-spiro[4.5]decan-4-one (Compound #20)

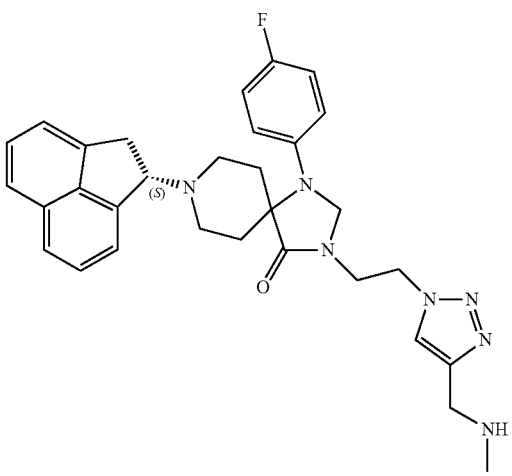

8-(R)-Acenaphthen-1-yl-1-(4-fluoro-phenyl)-3-[2-(4-methylaminomethyl-[1,2,3]triazol-1-yl)-ethyl]-1,3,8-triaza-spiro[4.5]decan-4-one was prepared according to the procedure as described in Example 14 above.
MS (ES$^+$) m/z 540.4 (M+H)$^+$.

EXAMPLE 20

8-(R)-Acenaphthen-1-yl-1-(4-fluoro-phenyl)-3-[2-(4-hydroxymethyl-[1,2,3]triazol-1-yl)-ethyl]-1,3,8-triaza-spiro[4.5]decan-4-one (Compound #22)

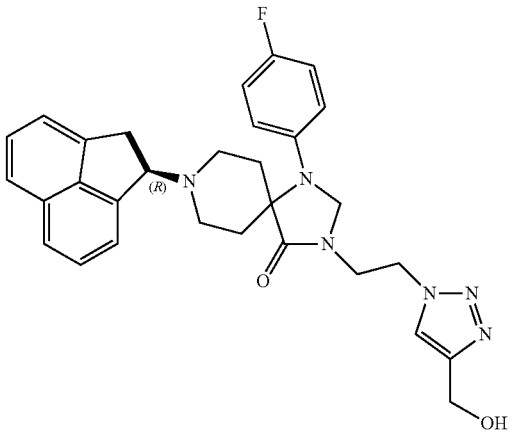

8-(R)-Acenaphthen-1-yl-1-(4-fluoro-phenyl)-3-[2-(4-hydroxymethyl-[1,2,3]triazol-1-yl)-ethyl]-1,3,8-triaza-spiro[4.5]decan-4-one was prepared according to the procedure as described in Example 14 above.
$^1$H NMR (400 MHz, CDCl$_3$) δ7.68-7.66 (1H, m), 7.61-7.59 (1H, m), 7.56 (1H, s), 7.52-7.42 (3H, m), 7.26-7.25 (1H, m), 7.00-6.96 (2H, m), 6.90-6.86 (2H, m), 4.92-4.89 (1H, m), 4.66 (2H, s), 4.60-4.57 (2H, m), 4.40-4.37 (2H, m), 3.89-3.81 (2H, m), 3.49-3.43 (1H, m), 3.38-3.32 (1H, m), 2.98-2.90 (2H, m), 2.75-2.72 (1H, m), 2.24-2.16 (1H, m), 2.11-2.03 (1H, m), 1.63-1.60 (1H, m), 1.56-1.52 (1H, m)

MS (ES$^+$) m/z 527.2 (M+H)$^+$.

EXAMPLE 21

8-(S)-Acenaphthen-1-yl-1-(4-fluoro-phenyl)-3-[2-(4-hydroxymethyl-[1,2,3]triazol-1-yl)-ethyl]-1,3,8-triaza-spiro[4.5]decan-4-one (Compound #23)

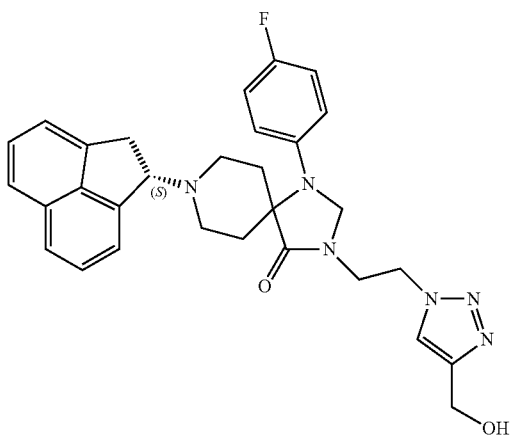

8-(S)-Acenaphthen-1-yl-1-(4-fluoro-phenyl)-3-[2-(4-hydroxymethyl-[1,2,3]triazol-1-yl)-ethyl]-1,3,8-triaza-spiro[4.5]decan-4-one was prepared according to the procedure as described in Example 14 above.

MS (ES$^+$) m/z 527.2 (M+H)$^+$.

EXAMPLE 22

8-(S)-Acenaphthen-1-yl-3-[2-(4-cyclopropyl-[1,2,3]triazol-1-yl)-ethyl]-1-(4-fluoro-phenyl)-1,3,8-triaza-spiro[4.5]decan-4-one (Compound #25)

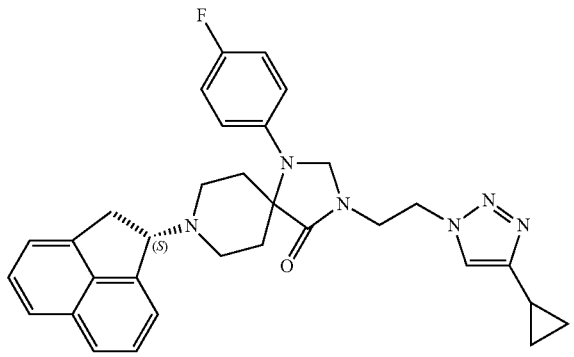

8-(S)-Acenaphthen-1-yl-3-[2-(4-cyclopropyl-[1,2,3]triazol-1-yl)-ethyl]-1-(4-fluoro-phenyl)-1,3,8-triaza-spiro[4.5]decan-4-one was prepared according to the procedure as described in Example 14 above.

$^1$H NMR (400 MHz, CDCl$_3$) δ7.68-7.66 (1H, m), 7.61-7.59 (1H, m), 7.53-7.47 (3H, m), 7.45-7.42 (1H, m), 7.26-7.25 (1H, m), 7.01-6.97 (2H, m), 6.89-6.86 (2H, m), 4.93-4.91 (1H, m), 4.56-4.53 (2H, m), 4.35-4.33 (2H, m), 3.90-3.82 (2H, m), 3.51-3.46 (1H, m), 3.38-3.32 (1H, m), 3.02-2.93 (2H, m), 2.77-2.74 (1H, m), 2.40-2.37 (1H, m), 2.23-2.16 (1H, m), 2.10-2.02 (1H, m), 1.85-1.78 (1H, m), 1.62-1.58 (1H, m), 1.53-1.49 (1H, m), 0.84-0.77 (2H, m), 0.75-0.69 (2H, m)

MS (ES$^+$) m/z 537.2 (M+H)$^+$.

EXAMPLE 23

8-(R)-Acenaphthen-1-yl-3-[2-(4-cyclopropyl-[1,2,3]triazol-1-yl)-ethyl]-1-(4-fluoro-phenyl)-1,3,8-triaza-spiro[4.5]decan-4-one (Compound #24)

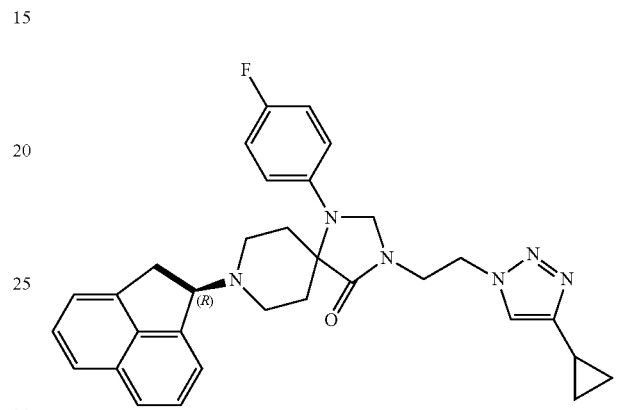

8-(R)-Acenaphthen-1-yl-3-[2-(4-cyclopropyl-[1,2,3]triazol-1-yl)-ethyl]-1-(4-fluoro-phenyl)-1,3,8-triaza-spiro[4.5]decan-4-one was prepared according to the procedure as described in Example 14 above.

MS (ES$^+$) m/z 537.2 (M+H)$^+$.

EXAMPLE 24

8-(R)-Acenaphthen-1-yl-1-(4-fluoro-phenyl)-3-[2-(4-methoxymethyl-[1,2,3]triazol-1-yl)-ethyl]-1,3,8-triaza-spiro[4.5]decan-4-one (Compound #26)

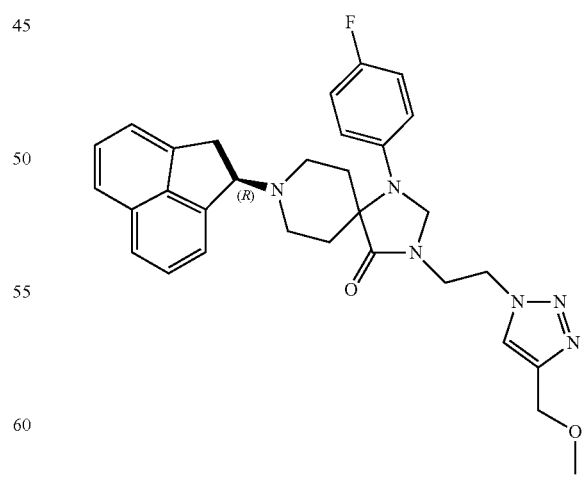

8-(R)-Acenaphthen-1-yl-1-(4-fluoro-phenyl)-3-[2-(4-methoxymethyl-[1,2,3]triazol-1-yl)-ethyl]-1,3,8-triaza-spiro[4.5]decan-4-one was prepared according to the procedure as described in Example 14 above.

¹H NMR (400 MHz, CDCl₃) δ7.68-7.66 (1H, m), 7.61-7.59 (1H, m), 7.56 (1H, s), 7.53-7.42 (3H, m), 7.27-7.25 (1H, m), 7.01-6.97 (2H, m), 6.90-6.86 (2H, m), 4.93-4.91 (1H, m), 4.63-4.61 (2H, m), 4.47 (2H, s), 4.38-4.35 (2H, m), 3.90-3.87 (2H, m), 3.50-3.45 (1H, m), 3.38-3.32 (1H, m), 3.29 (3H, s), 3.02-2.94 (2H, m), 2.77-2.74 (1H, m), 2.40-2.37 (1H, m), 2.26-2.19 (1H, m), 2.12-2.05 (1H, m), 1.66-1.62 (1H, m), 1.56-1.52 (1H, m)

MS (ES⁺) m/z 541.2 (M+H)⁺.

EXAMPLE 25

8-(S)-Acenaphthen-1-yl-1-(4-fluoro-phenyl)-3-[2-(4-methoxymethyl-[1,2,3]triazol-1-yl)-ethyl]-1,3,8-triaza-spiro[4.5]decan-4-one (compound #27)

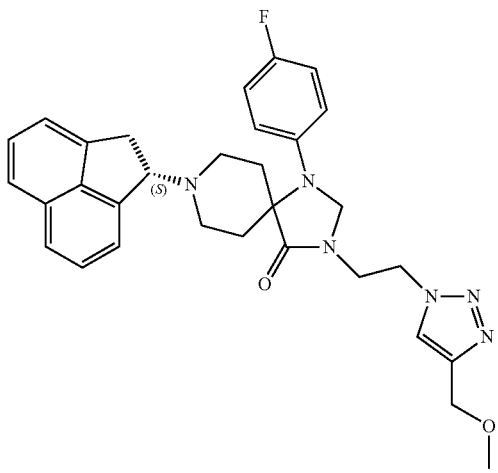

8-(S)-Acenaphthen-1-yl-1-(4-fluoro-phenyl)-3-[2-(4-methoxymethyl-[1,2,3]triazol-1-yl)-ethyl]-1,3,8-triaza-spiro[4.5]decan-4-one was prepared according to the procedure as described in Example 14 above.

MS (ES⁺) m/z 541.2 (M+H)⁺.

EXAMPLE 26

8-(R)-Acenaphthen-1-yl-3-[2-(4-dimethylaminomethyl-[1,2,3]triazol-1-yl)-ethyl]-1-(4-fluoro-phenyl)-1,3,8-triaza-spiro[4.5]decan-4-one (Compound #28)

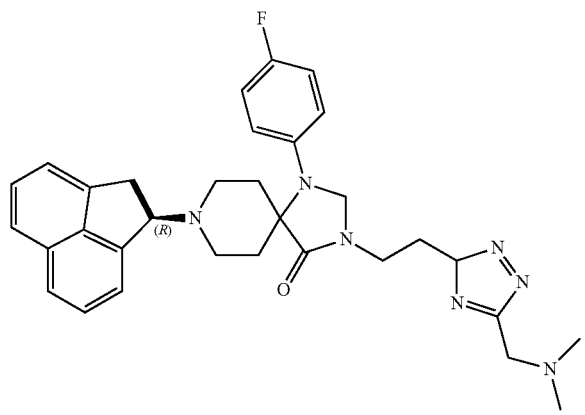

8-(R)-Acenaphthen-1-yl-3-[2-(4-dimethylaminomethyl-[1,2,3]triazol-1-yl)-ethyl]-1-(4-fluoro-phenyl)-1,3,8-triaza-spiro[4.5]decan-4-one was prepared according to the procedure as described in Example 14 above.

MS (ES⁺) m/z 554.2 (M+H)⁺.

EXAMPLE 27

8-(S)-Acenaphthen-1-yl-3-[2-(4-dimethylaminomethyl-[1,2,3]triazol-1-yl)-ethyl]-1-(4-fluoro-phenyl)-1,3,8-triaza-spiro[4.5]decan-4-one (Compound #29)

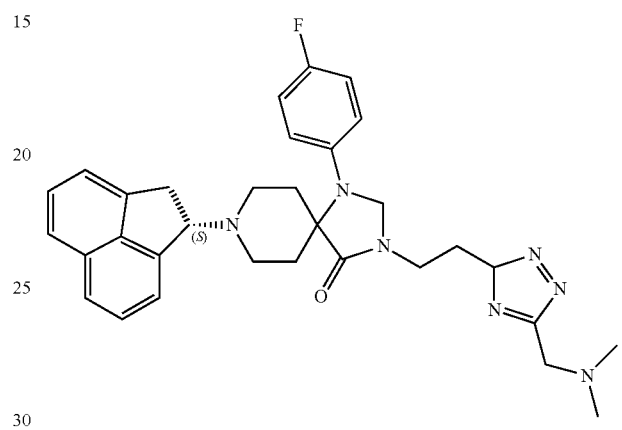

8-(S)-Acenaphthen-1-yl-3-[2-(4-dimethylaminomethyl-[1,2,3]triazol-1-yl)-ethyl]-1-(4-fluoro-phenyl)-1,3,8-triaza-spiro[4.5]decan-4-one was prepared according to the procedure as described in Example 14 above.

MS (ES⁺) m/z 554.2 (M+H)⁺.

EXAMPLE 28

Biological Assay: Affinity for the ORL-1 Receptor

The nociceptin receptor binding assay measures the binding of [Leucyl-3,4,5-³H]-nociceptin (90 Ci/mmol, Perkin Elmer) to the recombinant human nociceptin receptor (ORL-1, GeneBank Accession number X77130) on HEK293 cell membranes (Perkin-Elmer).

The cell membranes were thawed, reconstituted and homogenized 1:20 (v/v) in an assay buffer containing 50 mM HEPES, 1 mM EDTA and 10 mM MgCl₂ (pH 7.4). To a 96-well plate containing 50 μL/well of compound, 50 μL/well of membranes were added. Some wells contained 5 μM nociceptin to account for nonspecific binding. The radioligand was added at a 0.4 nM concentration in a volume of 100 μL/well. The mixture was incubated for 2 hours at 25° C. Following the incubation period, the samples were collected onto PEI-presoaked, glass-fiber 96-well filter plates using the Filtermate harvester (Perkin-Elmer). Each plate was washed nine times with ice-cold assay buffer to remove free radioligand. After drying, 30 μL/well of Microscint-20 (Perkin-Elmer) were added. The plates were sealed and counted on a Packard Top Count scintillation counter to determine membrane-bound radioactivity.

For each test compound, the total binding was measured at several concentrations and the IC₅₀ (the concentration at which 50% of the binding is inhibited) was determined from the graphical display of X=logarithm of concentration versus Y=response, using the following calculation:

$$Y = (\text{Minimum}) + \frac{(\text{Maximum} - \text{Minimum})}{(1 + 10^{\log(EC_{50}-X)})}$$

For some of the test compounds, the Ki was determined by nonlinear curve fitting using the Cheng-Prussoff equation:

$Ki = (IC_{50})/(+[\text{radioligand}]/Kd)$

For the ORL-1 binding, the Kd was 0.2 nM. The [radioligand] was the same as the Kd.

Representative compounds of the present invention were tested according to the procedure as described in Example 28 above, with results as listed in Table 3. (Note that for the compounds that were tested more than once, the value listed in Table 3 is the calculated mean.)

TABLE 3

ORL-1 Binding

| ID No. | ORL1 Ki (nM) |
| --- | --- |
| 1 | 1.54 |
| 8 | 4.00 |
| 9 | 0.08 |
| 12 | 0.30 |
| 13 | 0.76 |
| 14 | 1.20 |
| 15 | 1.01 |
| 16 | 0.23 |
| 17 | 0.28 |
| 18 | 0.98 |
| 19 | 0.33 |
| 20 | 0.20 |
| 21 | 0.07 |
| 22 | 0.33 |
| 23 | 0.93 |
| 24 | 0.50 |
| 25 | 0.89 |
| 26 | 0.05 |
| 27 | 0.37 |
| 28 | 0.30 |
| 29 | 0.81 |
| 30 | 1.37 |
| 31 | 0.38 |
| 32 | 0.59 |
| 33 | >1 |
| 34 | 0.08 |
| 35 | 0.21 |
| 36 | 1.24 |
| 37 | 4.96 |
| 38 | 0.99 |
| 39 | 2.20 |
| 40 | 0.80 |
| 41 | 3.36 |

EXAMPLE 29

Biological Assays: Rat Brain Delta Opioid Receptor Binding

Male, Sprague Dawley rats (150-250 g, VAF, Charles River, Kingston, N.Y.) were euthanized using $CO_2$, and their brains were removed and were placed immediately in ice-cold Tris HCl buffer (50 mM, pH 7.4). The forebrains were separated from the remainder of the brain by a coronal transsection, beginning dorsally at the colliculi and passing ventrally through the midbrain-pontine junction. After dissection, the forebrains were homogenized in approximately 30 mls of Tris HCl buffer in a Teflon®-glass homogenizer. The homogenate was centrifuged at 40,000×g for 15 min and the supernatant was discarded. With several brief pulses from a Polytron homogenizer, the pellet was re-suspended at a concentration of 1 g of forebrain tissue per 80 mL Tris HCl buffer containing 5 mM $MgCl_2$. This particulate preparation was used for the delta opioid binding assays. Following incubation with the delta selective peptide ligand ~0.1 nM [$^3$H] Naltrindole at 25° C. for 2.5 h in a 96-well plate with total volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×50 μL of Betaplate Scint scintillation fluid (LKB) was added and the radioactivity quantified on a LKB (Wallac) 1205 BetaPlate liquid scintillation counter.

The data from the scintillation counter were used to calculate either the % inhibition compared to control binding (when only a single concentration of test compound was evaluated) or a $K_i$ value (when a range of concentrations was tested).

Percent inhibition was calculated as follow: % Inhibition= [(total dpm–test compound dpm)/(total dpm–nonspecific dpm)]×100. Kd and Ki values were calculated using Graph-Pad PRISM data analysis program.

EXAMPLE 30

Biological Assays: Rat Brain Mupioid Receptor Binding

Male, Sprague Dawley rats (150-250 g, VAF, Charles River, Kingston, N.Y.) were euthanized using $CO_2$, and their brains were removed and were placed immediately in ice-cold Tris HCl buffer (50 mM, pH 7.4). The forebrains were separated from the remainder of the brain by a coronal transection, beginning dorsally at the colliculi and passing ventrally through the midbrain-pontine junction. After dissection, the forebrains were homogenized in approximately 30 mls of Tris HCl buffer in a Teflon®-glass homogenizer. The homogenate was centrifuged at 40,000×g for 15 min and the supernatant was discarded. With several brief pulses from a Polytron homogenizer, the pellet was resuspended at a concentration of 1 g of forebrain tissue per 80 mL Tris HCl buffer containing 5 mM $MgCl_2$. This particulate preparation was used for the delta opioid binding assays. Following incubation with the mu selective peptide ligand, ~0.8 nM [$^3$H] DAMGO, at 25° C. for 2.5 h in a 96-well plate with total assay volume of 1 mL, the plate contents were filtered through Wallac filtermat B sheets on a Tomtec 96-well harvester. The filters were rinsed three times with 2 mL of 10 mM HEPES (pH 7.4), and dried in a 650 W microwave oven for 1.75 min twice. To each sample area 2×40 μL of Betaplate Scint scintillation fluid (LKB) was added and the radioactivity quantified on a LKB (Wallac) 1205 BetaPlate liquid scintillation counter.

The data from the scintillation counter were used to calculate either the % inhibition compared to control binding (when only a single concentration of test compound was evaluated) or a $K_i$ value (when a range of concentrations tested).

Percent inhibition was calculated as follow: % Inhibition= [(total dpm–test compound dpm)/(total dpm–nonspecific dpm)]×100. Kd and Ki values were calculated using Graph-Pad PRISM data analysis program.

Representative compounds of the present invention were tested according to the procedure as described in Examples 29 and 30 above, with results as listed in Table 4. (Note that for the compounds which were tested more than once, the value listed in Table 4 is the calculated mean.)

TABLE 4

| ID No. | Delta % Inh @ 1 μM | Delta Ki (nM) | Mu % Inh @ 1 μM | Mu Ki (nM) |
|---|---|---|---|---|
| 1 | 39 | | 94 | |
| 8 | 20 | | 95 | 46.02 |
| 9 | | | | 5.42 |
| 19 | | | | 15.60 |
| 20 | | 2979.00 | | 168.60 |
| 21 | | 862.80 | | 59.68 |
| 22 | | | | 5.05 |
| 24 | | | | 4.63 |
| 26 | | | | 3.91 |
| 27 | | | | 17.92 |
| 28 | | | | 9.25 |
| 29 | | | | 34.99 |
| 31 | | 173.05 | | 38.55 |
| 32 | | | | 8.88 |
| 34 | | 1510.50 | | 82.28 |
| 35 | | | | 18.02 |
| 36 | | | | 41.36 |
| 38 | | | | 66.72 |
| 39 | | | | 120.30 |
| 40 | | | | 13.67 |

EXAMPLE 31

Kappa (KOP) Receptor Binding (In Vitro)

The assay evaluated the affinity of a test compound for the agonist site of the kappa opioid receptor in the guinea pig cerebellum, as determined in a radioligand binding assay.
Procedure The membranes homogenates of cerebellum (250 μg of protein) were incubated for 80 min at 22° C. with 0.7 nM [$^3$H]U-69593 in the absence or presence of the test compound in a buffer containing 50 mM Tris-HCl (pH=7.4), 10 mM MgCl$_2$ and 1 mM EDTA. Non-specific binding was determined in the presence of 10 μM naloxone.

Following incubation, the sample(s) were filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters were dried, and then counted for radioactivity in a scintillation counter (Topcount, Packard) using a scintillation cocktail (Microscint 0, Packard). The results (below) are expressed as a percent inhibition of the control radioligand specific binding.

The standard reference compound used was U-50488, which was tested in each experiment at several concentrations to obtain a competition curve from which its IC$_{50}$ is calculated. (Kinouchi, K. and Pasternak, G. W. (1991) Evidence for K1 opioid receptor multiplicity in the guinea pig cerebellum, Eur. J. Pharmacol., 207:135.)
Analysis The specific ligand binding to the receptors was defined as the difference between the total binding and the non-specific binding determined in the presence of an excess of unlabelled ligand.

The results below are expressed as a percent of control specific binding ((measured specific binding/control specific binding)×100) and as a percent inhibition of control specific binding (100−((measured specific binding/control specific binding)×100)) obtained in the presence of the test compounds.

The IC$_{50}$ values (concentration causing a half-maximal inhibition of control specific binding) and Hill coefficients (nH) were determined by non-linear regression analysis of the competition curves generated with mean replicate values using Hill equation curve fitting ($Y=D+[(A-D)/(1+(C/C_{50})^{nH})]$, where Y=specific binding, D=minimum specific binding, A=maximum specific binding, C=compound concentration, $C_{50}$=IC$_{50}$, and nH=slope factor). This analysis was performed using a software developed at Cerep (Hill software) and validated by comparison with data generated by the commercial software SigmaPlot® 4.0 for Windows® (© 1997 by SPSS Inc.).

The inhibition constants (Ki) were calculated using the Cheng Prusoff equation ($Ki=IC_{50}/(1+(L/K_D))$, where L=concentration of radioligand in the assay, and $K_D$=affinity of the radioligand for the receptor).

Representative compounds of the present invention were tested according to the procedure outlined above with results as listed in Table 5 below.

TABLE 5

| ID No. | Kappa Binding Kappa Ki (nM) |
|---|---|
| 31 | 94 |
| 20 | 68 |
| 21 | 45 |

EXAMPLE 32

As a specific embodiment of an oral composition, 100 mg of the compound prepared as in Example 19 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

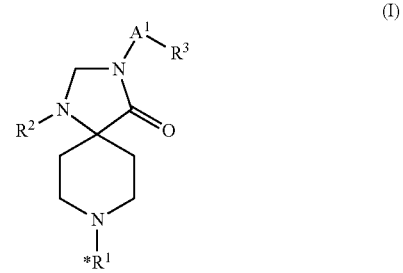

wherein

R$^1$ is 1-acenaphthenyl;

R$^2$ is 4-fluorophenyl;

A$^1$ is selected from the group consisting of —CH$_2$—, —CH$_2$CH$_2$—, —CH$_2$CH$_2$CH$_2$— and —CH$_2$CH$_2$CH$_2$CH$_2$—;

$R^3$ is selected from the group consisting of

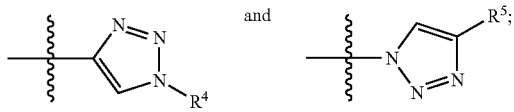

and wherein $R^4$ is selected from the group consisting of hydroxy, cycloalkyl, phenyl, benzyl, imidazolyl, pyridyl, —$C_{1-4}$alkyl-$NR^AR^B$, —$C_{1-4}$alkyl-OH, —$C_{1-4}$alkyl-O—$C_{1-4}$alkyl, —C(O)OH and —C(O)O—$C_{1-4}$alkyl;

wherein the phenyl, imidazolyl or pyridyl, is optionally substituted with one or more substituents independently selected from the group consisting of halogen and $C_{1-4}$alkyl;

wherein $R^A$ and $R^B$ are each independently selected from the group consisting of hydrogen and $C_{1-4}$alkyl;

and wherein $R^5$ is selected from the group consisting of hydroxy, cycloalkyl, phenyl, benzyl, imidazolyl, pyridyl, —$C_{1-4}$alkyl-$NR^CR^D$, —$C_{1-4}$alkyl-OH, —$C_{1-4}$alkyl-O—$C_{1-4}$alkyl, —C(O)OH and —C(O)O—$C_{1-4}$alkyl;

wherein the phenyl, imidazolyl or pyridyl, is optionally substituted with one or more substituents independently selected from the group consisting of halogen and $C_{1-4}$alkyl;

and wherein $R^C$ and $R^D$ are each independently selected from the group consisting of hydrogen and $C_{1-4}$alkyl; or a pharmaceutically acceptable salt thereof.

2. A compound as in claim 1, wherein
$R^1$ is 1-acenaphthenyl;
$R^2$ is 4-fluorophenyl;
$A^1$ is selected from the group consisting of —$CH_2CH_2$—, —$CH_2CH_2CH_2$— and —$CH_2CH_2CH_2CH_2$—;
$R^3$ is selected from the group consisting of

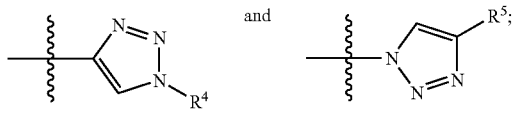

and wherein $R^4$ is selected is selected from the group consisting of hydroxy, $C_{3-8}$cycloalkyl, phenyl, benzyl, imidazolyl, pyridyl, —$C_{1-4}$alkyl-$NR^AR^B$, —$C_{1-4}$alkyl-OH, —$C_{1-4}$alkyl-O—$C_{1-4}$alkyl, and —C(O)O—$C_{1-4}$alkyl;

wherein the phenyl, imidazolyl or pyridyl, is optionally substituted with one to two substituents independently selected from the group consisting of halogen and $C_{1-4}$alkyl;

and wherein $R^A$ and $R^B$ are each independently selected from the group consisting of hydrogen and $C_{1-4}$alkyl;

wherein $R^5$ is selected from the group consisting of hydroxy, $C_{3-8}$cycloalkyl, phenyl, benzyl, imidazolyl, pyridyl, —$C_{1-4}$alkyl-$NR^CR^D$, —$C_{1-4}$alkyl-OH, —$C_{1-4}$alkyl-O—$C_{1-4}$alkyl, and —C(O)O—$C_{1-4}$alkyl;

wherein the phenyl, imidazolyl or pyridyl, is optionally substituted with one to two substituents independently selected from the group consisting of halogen and $C_{1-4}$alkyl;

and wherein $R^C$ and $R^D$ are each independently selected from the group consisting of hydrogen and $C_1$-4alkyl;

or a pharmaceutically acceptable salt thereof.

3. A compound as in claim 2, wherein
$R^1$ is 1-acenaphthenyl;
$R^2$ is 4-fluorophenyl;
$A^1$ is selected from the group consisting of —$CH_2CH_2$— and —$CH_2CH_2CH_2$—;
$R^3$ is selected from the group consisting of

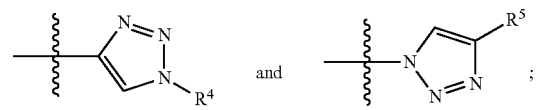

wherein $R^4$ is selected from the group consisting of hydroxy, $C_{3-8}$cycloalkyl, phenyl, benzyl, imidazolyl, pyridyl, —$C_{1-2}$alkyl-$NR^AR^B$, —$C_{1-2}$alkyl-OH, —$C_{1-2}$alkyl-O—$C_{1-2}$alkyl and —C(O)O—$C_{1-2}$alkyl;

wherein the phenyl or imidazolyl is optionally substituted with substituent selected from the group consisting of halogen and $C_{1-2}$alkyl; and wherein $R^A$ and $R^B$ are each independently selected from the group consisting of hydrogen and $C_{1-2}$alkyl;

and wherein $R^5$ is selected from the group consisting of hydroxy, $C_{3-8}$cycloalkyl, phenyl, benzyl, imidazolyl, pyridyl, —$C_{1-2}$alkyl-$NR^CR^D$, —$C_{1-2}$alkyl-OH, —$C_{1-2}$alkyl-O—$C_{1-2}$alkyl and —C(O)O—$C_{1-2}$alkyl;

wherein the phenyl or imidazolyl is optionally substituted with substituent selected from the group consisting of halogen and $C_{1-2}$alkyl; and wherein $R^C$ and $R^D$ are each independently selected from the group consisting of hydrogen and $C_{1-2}$alkyl;

or a pharmaceutically acceptable salt thereof.

4. A compound as in claim 3, wherein
$R^1$ is 1-acenaphthenyl;
$R^2$ is 4-fluorophenyl;
$A^1$ is selected from the group consisting of —$CH_2CH_2$— and —$CH_2CH_2CH_2$—;
$R^3$ is selected from the group consisting of 4-(1-benzyl-1,2,3-triazolyl), 1-(4-(methylaminomethyl-1,2,3-triazolyl), 1-(4-hydroxy-1,2,3-triazolyl), 1-(4-cyclopropyl-1,2,3-triazolyl), 1-(4-(methoxymethyl)-1,2,3-triazolyl), 1-(4-(dimethylaminomethyl)-1,2,3-triazolyl), 1-(4-(3-fluorophenyl)-1,2,3-triazolyl), 1-(4-(hydroxymethyl)-1,2,3-triazolyl), 1-(4-(ethoxycarbonyl)-1,2,3-triazolyl), 1-(4-(2-(1-methyl-imidazolyl))-1,2,3-triazolyl) and 1-(4-(3-pyridyl)-1,2,3-triazolyl);

or a pharmaceutically acceptable salt thereof.

5. A compound as in claim 4, wherein
$R^1$ is 1-acenaphthenyl;
$R^2$ is 4-fluorophenyl;
$A^1$ is selected from the group consisting of —$CH_2CH_2$— and —$CH_2CH_2CH_2$—;
$R^3$ is selected from the group consisting of 1-(4-(methylaminomethyl-1,2,3-triazolyl), 1-(4-hydroxy-1,2,3-triazolyl), 1-(4-cyclopropyl-1,2,3-triazolyl), 1-(4-(methoxymethyl)-1,2,3-triazolyl), 1-(4-(dimethylaminomethyl)-1,2,3-triazolyl), 1-(4-(3-fluorophenyl)-1,2,3-triazolyl), 1-(4-(hydroxymethyl)-1,2,3-triazolyl), 1-(4-(2-(1-methyl-imidazolyl))-1,2,3-triazolyl) and 1-(4-(3-pyridyl)-1,2,3-triazolyl);

or a pharmaceutically acceptable salt thereof.

6. A compound as in claim 4, wherein
$R^1$ is 1-acenaphthenyl;
$R^2$ is 4-fluorophenyl;
$A^1$ is selected from the group consisting of —$CH_2CH_2$— and —$CH_2CH_2CH_2$—;

R³ is selected from the group consisting of 1-(4-(methylaminomethyl-1,2,3-triazolyl), 1-(4-hydroxy-1,2,3-triazolyl), 1-(4-(methoxymethyl)-1,2,3-triazolyl), 1-(4-(dimethylaminomethyl)-1,2,3-triazolyl) and 1-(4-(3-fluorophenyl)-1,2,3-triazolyl);
or a pharmaceutically acceptable salt thereof.

7. A compound as in claim 4, wherein
R¹ is 1-acenaphthenyl;
R² is 4-fluorophenyl;
A¹ is selected from the group consisting of —CH₂CH₂— and —CH₂CH₂CH₂—;
R³ is selected from the group consisting of 1-(4-(methylaminomethyl-1,2,3-triazolyl) and 1-(4-(methoxymethyl)-1,2,3-triazolyl);
or a pharmaceutically acceptable salt thereof.

8. A compound as in claim 4, wherein R¹ is 1-acenaphthenyl; R² is 4-fluorophenyl; A¹ is selected from the group consisting of —CH₂CH₂— and —CH₂CH₂CH₂—; and R³ is 4-(1-benzyl-1,2,3-triazolyl) or a pharmaceutically acceptable salt thereof.

9. A compound as in claim 4, wherein the compound of formula (I) is present in an enantiomer excess of greater than or equal to about 95% of the S-enantiomer.

10. A compound as in claim 4, wherein the compound of formula (I) is present in an enantiomer excess of greater than or equal to about 95% of the R-enantiomer.

11. A compound of formula (II)

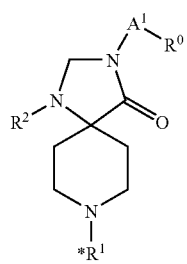

(II)

wherein
R¹ is 1-acenaphthenyl;
R² is 4-fluorophenyl;
A¹ is selected from the group consisting of —CH₂—, —CH₂CH₂—, —CH₂CH₂CH₂— and —CH₂CH₂CH₂CH₂—;
R⁰ is selected from the group consisting of —CCH, —N₃, —O—SO₂—C₁₋₄alkyl, —O-(2-tetrahydropyranyl);
or a pharmaceutically acceptable salt thereof.

12. A compound as in claim 11, wherein
R¹ is 1-acenaphthenyl;
R² is 4-fluorophenyl;
A¹ is selected from the group consisting of —CH₂CH₂— and —CH₂CH₂CH₂—;
R⁰ is selected from the group consisting of —CCH, —N₃, —O—SO₂—CH₃ and —O-(2-tetrahydrodpyranyl);
or a pharmaceutically acceptable salt thereof.

13. A compound as in claim 12, wherein
R¹ is 1-acenaphthenyl;
R² is 4-fluorophenyl;
A¹ is selected from the group consisting of —CH₂CH₂— and —CH₂CH₂CH₂—;
R⁰ is selected from the group consisting of —N₃, and —O-(2-tetrahydrodpyranyl);
or a pharmaceutically acceptable salt thereof.

14. A pharmaceutical composition comprising a pharmaceutically acceptable carrier and a compound of claim 1.

15. A pharmaceutical composition made by mixing a compound of claim 1 and a pharmaceutically acceptable carrier.

16. A process for making a pharmaceutical composition comprising mixing a compound of claim 1 and a pharmaceutically acceptable carrier.

17. A method of treating a disorder mediated by the ORL-1 receptor, in a subject in need thereof comprising administering to the subject a therapeutically effective amount of the compound of claim 1, wherein the disorder mediated by the ORL-1 receptor is selected from the group consisting of anxiety, substance abuse, asthma, and epilepsy.

18. The method of claim 17, wherein the disorder mediated by the ORL-1 receptor is anxiety.

19. A method of treating a disorder mediated by the ORL-1 receptor, in a subject in need thereof comprising administering to the subject a therapeutically effective amount of the composition of claim 14, wherein the disorder mediated by the ORL-1 receptor is selected from the group consisting of anxiety, substance abuse, asthma, and epilepsy.

20. A method of treating a condition selected from the group consisting of anxiety, substance abuse, asthma, and epilepsy in a subject in need thereof comprising administering to the subject a therapeutically effective amount of the compound of claim 1.

21. A method of treating a condition selected from the group consisting of anxiety, -substance abuse, asthma, and epilepsy, in a subject in need thereof comprising administering to the subject a therapeutically effective amount of the composition of claim 14.

22. A pharmaceutical composition comprising a pharmaceutically acceptable carrier and a compound of claim 11.

23. A pharmaceutical composition made by mixing a compound of claim 11 and a pharmaceutically acceptable carrier.

24. A process for making a pharmaceutical composition comprising mixing a compound of claim 11 and a pharmaceutically acceptable carrier.

25. A method of treating a disorder mediated by the ORL-1 receptor, in a subject in need thereof comprising administering to the subject a therapeutically effective amount of the compound of claim 11, wherein the disorder mediated by the ORL-1 receptor is selected from the group consisting of anxiety, substance abuse, asthma, and epilepsy.

26. The method of claim 25, wherein the disorder mediated by the ORL-1 receptor is anxiety.

27. A method of treating a disorder mediated by the ORL-1 receptor, in a subject in need thereof comprising administering to the subject a therapeutically effective amount of the composition of claim 22 wherein the disorder mediated by the ORL-1 receptor is selected from the group consisting of anxiety, substance abuse, asthma, and epilepsy.

28. A method of treating a condition selected from the group consisting of anxiety, substance abuse, asthma, and epilepsy, in a subject in need thereof comprising administering to the subject a therapeutically effective amount of the compound of claim 11.

29. A method of treating a condition selected from the group consisting of anxiety substance abuse, asthma, and epilepsy, in a subject in need thereof comprising administering to the subject a therapeutically effective amount of the composition of claim 22.

30. A process for the preparation of a compound of formula (Ia)

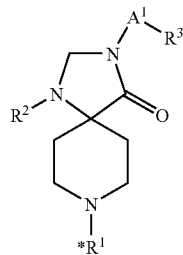

wherein
R¹ is 1-acenaphthenyl;
R² is 4-fluorophenyl;
A¹ is selected from the group consisting of —CH₂—, —CH₂CH₂—, —CH₂CH₂CH₂— and —CH₂CH₂CH₂CH₂—;
R³ is

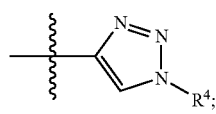

wherein R⁴ is selected from the group consisting of hydroxy, cycloalkyl, phenyl, benzyl, imidazolyl, pyridyl, —C₁₋₄alkyl-NR$^A$R$^B$, —C₁₋₄alkyl-OH, —C₁₋₄alkyl-O—C₁₋₄alkyl, —C(O)OH and —C(O)O—C₁₋₄alkyl;
wherein the phenyl, imidazolyl or pyridyl, is optionally substituted with one or more substituents independently selected from the group consisting of halogen and C₁₋₄alkyl;
and wherein R$^A$ and R$^B$ are each independently selected from the group consisting of hydrogen and C₁₋₄alkyl; or a pharmaceutically acceptable salt thereof;
comprising

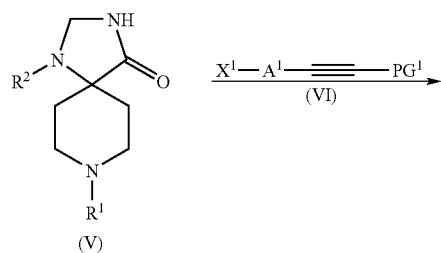

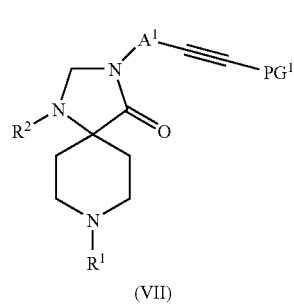

reacting a compound of formula (V) with a compound of formula (VI), wherein X¹ is a leaving group and wherein PG¹ is a protecting group, in the presence of a base, in an organic solvent, to yield the corresponding compound of formula (VII);

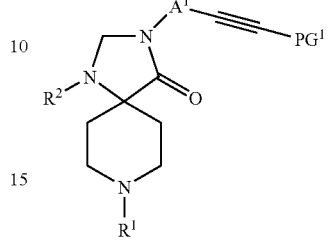

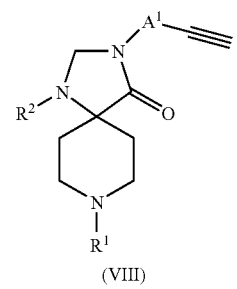

(VIII)

de-protecting the compound of formula (VII), to yield the corresponding compound of formula (VIII);

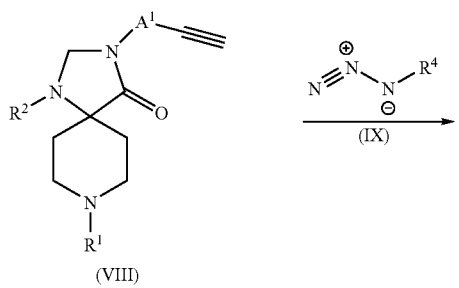

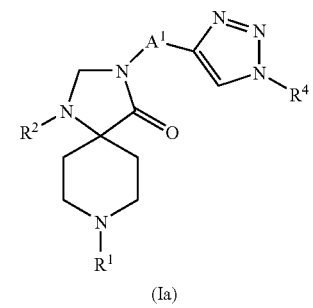

(Ia)

reacting the compound of formula (VIII) with a compound of formula (IX), in the presence of a copper (I) source, in the presence of a base, in an organic solvent, to yield the corresponding compound of formula (Ia).

31. A process for the preparation of a compound of formula (Ia)

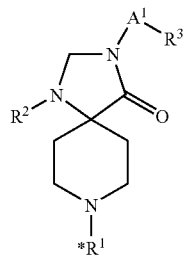

(Ia)

wherein

R$^1$ is 1-acenaphthenyl;

R$^2$ is 4-fluorophenyl;

A$^1$ is selected from the group consisting of —CH$_2$—, —CH$_2$CH$_2$—, —CH$_2$CH$_2$CH$_2$— and —CH$_2$CH$_2$CH$_2$CH$_2$—;

R$^3$ is

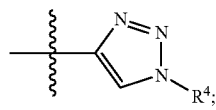

wherein R$^4$ is selected from the group consisting of hydroxy, cycloalkyl, phenyl, benzyl, imidazolyl, pyridyl, —C$_{1-4}$alkyl-NR$^A$R$^B$, —C$_{1-4}$alkyl-OH, —C$_{1-4}$alkyl-O—C$_{1-4}$alkyl, —C(O)OH and —C(O)O—C$_{1-4}$alkyl;

wherein the phenyl, imidazolyl or pyridyl, is optionally substituted with one or more substituents independently selected from the group consisting of halogen and C$_{1-4}$alkyl; and wherein R$^A$ and R$^B$ are each independently selected from the group consisting of hydrogen and C$_{1-4}$-alkyl;

or a pharmaceutically acceptable salt thereof;

comprising

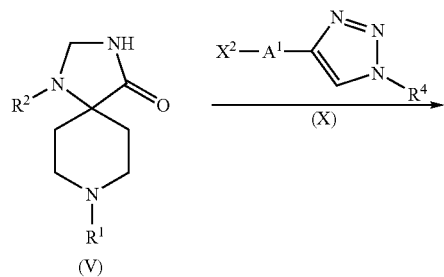

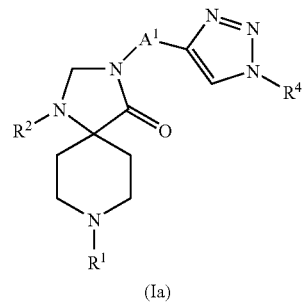

(Ia)

reacting a compound of formula (V), with a compound of formula (X), wherein X$^2$ is a leaving group, in the presence of a base, in an organic solvent, to yield the corresponding compound of formula (Ia).

32. A process for the preparation of a compound of formula (Ib)

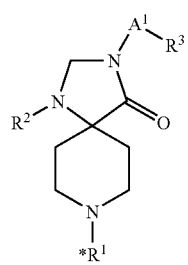

(Ib)

wherein

R$^1$ is 1-acenaphthenyl;

R$^2$ is 4-fluorophenyl;

A$^1$ is selected from the group consisting of —CH$_2$—, —CH$_2$CH$_2$—, —CH$_2$CH$_2$CH$_2$— and —CH$_2$CH$_2$CH$_2$CH$_2$—;

R$^3$ is

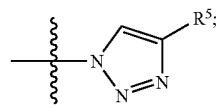

wherein R$^5$ is selected from the group consisting of hydroxy, cycloalkyl, phenyl, benzyl, imidazolyl, pyridyl, —C$_{1-4}$alkyl-NR$^C$R$^D$, —C$_{1-4}$alkyl-OH, —C$_{1-4}$alkyl-O—C$_{1-4}$alkyl, —C(O)OH and —C(O)O—C$_{1-4}$alkyl;

wherein the phenyl, imidazolyl or pyridyl, is optionally substituted with one or more substituents independently selected from the group consisting of halogen and C$_{1-4}$alkyl;

and wherein R$^C$ and R$^D$ are each independently selected from the group consisting of hydrogen and C$_{1-4}$alkyl;

or a pharmaceutically acceptable salt thereof;
comprising

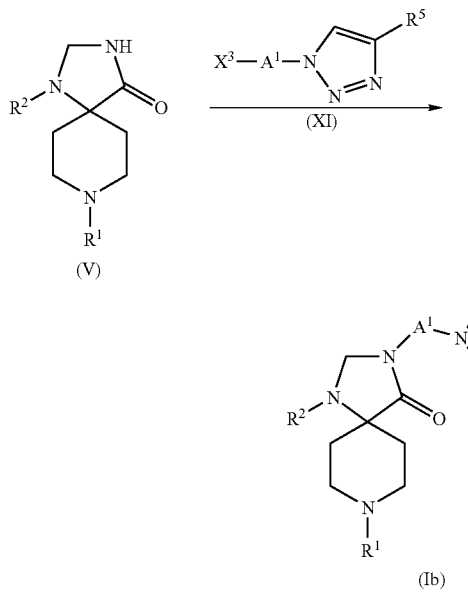

reacting a compound of formula (V), with a compound of formula (XI), wherein $X^3$ is a leaving group, in the presence of a base, in an organic solvent, to yield the corresponding compound of formula (Ib).

33. A process for the preparation of a compound of formula (Ib)

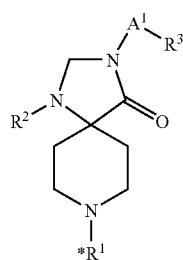
(Ib)

wherein
$R^1$ is 1-acenaphthenyl;
$R^2$ is 4-fluorophenyl;
$A^1$ is selected from the group consisting of —CH$_2$—, —CH$_2$CH$_2$—, —CH$_2$CH$_2$CH$_2$— and —CH$_2$CH$_2$CH$_2$CH$_2$—;
$R^3$ is

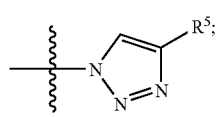

wherein $R^5$ is selected from the group consisting of hydroxy, cycloalkyl, phenyl, benzyl, imidazolyl, pyridyl, —C$_{1-4}$alkyl-NR$^C$R$^D$, —C$_{1-4}$alkyl-OH, —C$_{1-4}$alkyl-O—C$_{1-4}$alkyl, —C(O)OH and —C(O)O—C$_{1-4}$alkyl;

wherein the phenyl, imidazolyl or pyridyl, is optionally substituted with one or more substituents independently selected from the group consisting of halogen and C$_{1-4}$alkyl;
and wherein R$^C$ and R$^D$ are each independently selected from the group consisting of hydrogen and C$_{1-4}$alkyl;
or a pharmaceutically acceptable salt thereof;
comprising

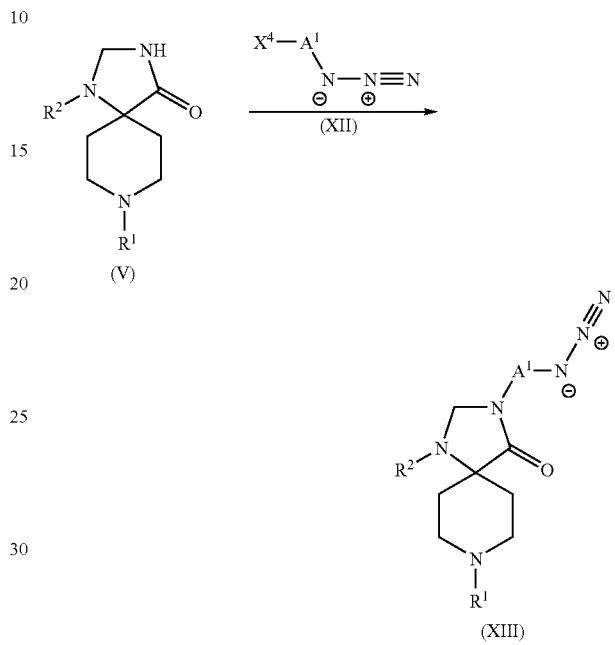

reacting a compound of formula (V), with a compound of formula (XII), wherein $X^4$ is a leaving group, in the presence of a base, in an organic solvent, to yield the corresponding compound of formula (XIII);

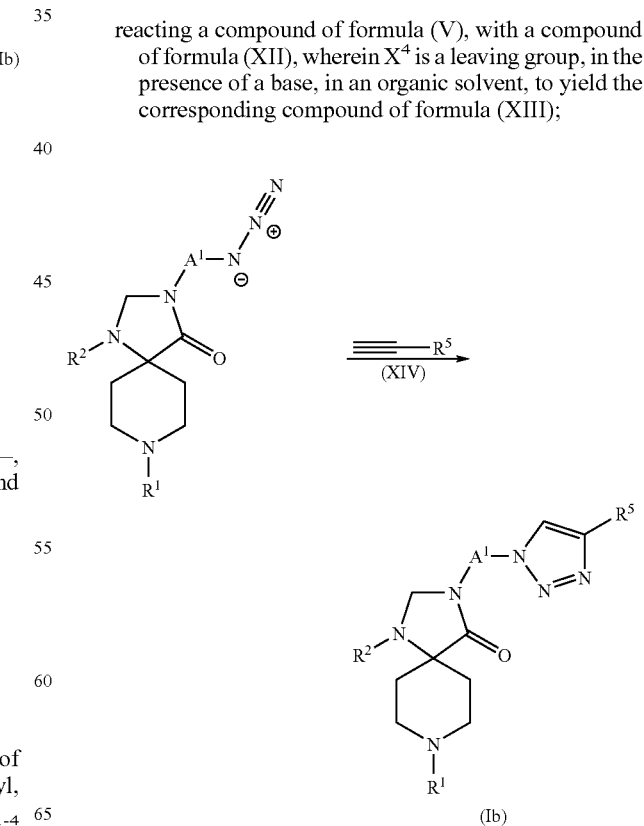

reacting the compound of formula (XIII) with a compound of formula (XIV), in the presence of a copper (I) source, in the presence of a base, in an organic solvent, to yield the corresponding compound of formula (Ib).

34. A process for the preparation of a compound of formula (Ib)

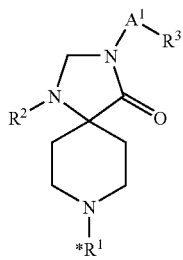
(Ib)

wherein $R^1$ is 1-acenaphthenyl;

$R^2$ is 4-fluorophenyl;

$A^1$ is selected from the group consisting of —CH$_2$—, —CH$_2$CH$_2$—, —CH$_2$CH$_2$CH$_2$— and —CH$_2$CH$_2$CH$_2$CH$_2$—;

$R^3$ is

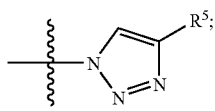

wherein $R^5$ is selected from the group consisting of hydroxy, cycloalkyl, phenyl, benzyl, imidazolyl, pyridyl, —C$_{1-4}$alkyl-NR$^C$R$^D$, —C$_{1-4}$alkyl-OH, —C$_{1-4}$alkyl-O—C$_{1-4}$alkyl, —C(O)OH and —C(O)O—C$_{1-4}$alkyl;

wherein the phenyl, imidazolyl or pyridyl, is optionally substituted with one or more substituents independently selected from the group consisting of halogen and C$_{1-4}$alkyl;

and wherein $R^C$ and $R^D$ are each independently selected from the group consisting of hydrogen and C$_{1-4}$alkyl;

or a pharmaceutically acceptable salt thereof;

comprising

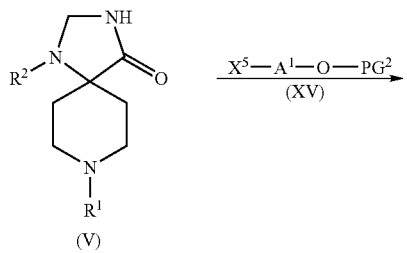

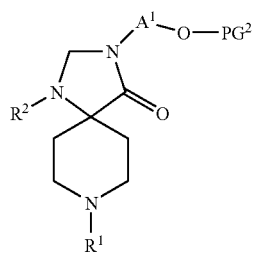

reacting a compound of formula (V), with a compound of formula (XV), wherein $X^5$ is a leaving group, and wherein PG$^2$ is a protecting group, in the presence of a base, in an organic solvent, to yield the corresponding compound of formula (XVI);

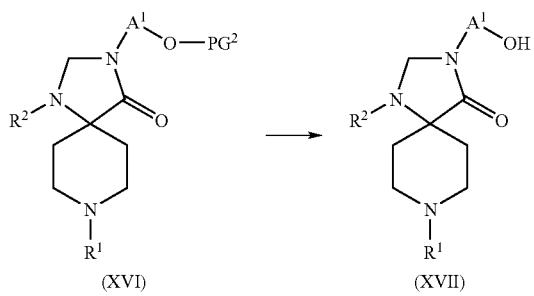

de-protecting the compound of formula (XVI) to yield the corresponding compound of formula (XVII);

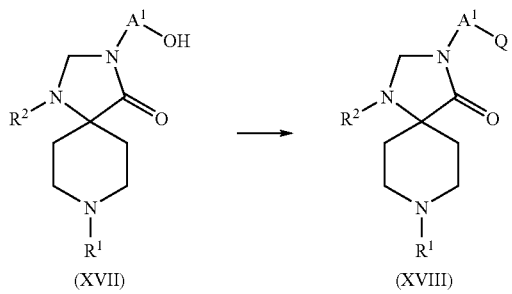

reacting the compound of formula (XVII) with a reagent which can introduce a nucleophilic leaving group, in an organic solvent, to yield the corresponding compound of formula (XVIII), wherein Q is the corresponding nucleophilic leaving group;

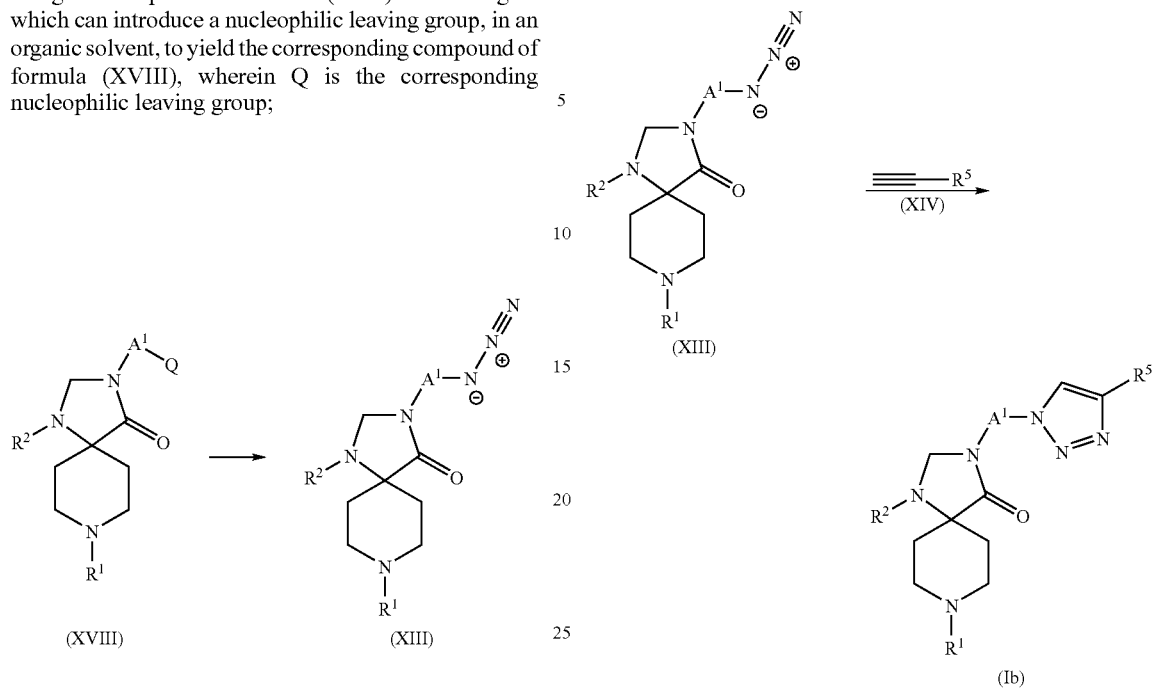

reacting the compound of formula (XVIII) with a source of azide (N₃), in an organic solvent, to yield the corresponding compound of formula (XIII);

reacting the compound of formula (XIII) with a compound of formula (XIV), in the presence of a copper (I) source, in the presence of a base, in an organic solvent, to yield the corresponding compound of formula (Ib).

\* \* \* \* \*